United States Patent
Neufeld et al.

(12) 
(10) Patent No.: US 6,589,782 B1
(45) Date of Patent: *Jul. 8, 2003

(54) ANGIOGENIC FACTOR AND USE THEREOF IN TREATING CARDIOVASCULAR DISEASE

(75) Inventors: Gera Neufeld, Haifa (IL); Eli Keshet, Kiryet Lam (IL); Israel Vlodavsky, Meraseret Zion (IL); Zoya Poltorak, Jerusalem (IL)

(73) Assignee: Technion Research & Development Co., Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/428,909

(22) Filed: Oct. 28, 1999

Related U.S. Application Data

(62) Division of application No. 08/784,551, filed on Jan. 21, 1997, now Pat. No. 6,013,780.
(60) Provisional application No. 60/025,537, filed on Sep. 6, 1996.

(51) Int. Cl.[7] .................. C12N 15/63; C12N 15/85; A61K 48/00; C07H 21/04
(52) U.S. Cl. .................. 435/320.1; 435/325; 435/455; 424/93.2; 424/93.21; 514/44; 536/23.1
(58) Field of Search .................. 536/23.1; 435/320.1, 435/325, 455; 514/44; 424/93.2, 93.21

(56) References Cited

U.S. PATENT DOCUMENTS 5,194,596 A * 3/1993 Tischer et al. .............. 530/399
6,013,780 A * 1/2000 Neufeld et al. ............. 536/23.1

OTHER PUBLICATIONS

Park; Abstract: Vascular endothelial growth factor, 1993.*
Verma et.al.; Gene therapy–promises,problems and prospects, 1997, Nature, vol. 389:239–242.*
Marshall; Gene Therapy's Growing Pains, 1995, Science, vol. 269: 1050–1055.*
Orkin et.al.; Report and Recommendations of the Panel to Assess the NIH Investment in Research on Gene Therapy, 1995.*

* cited by examiner

Primary Examiner—Anne M. Wehbé
(74) Attorney, Agent, or Firm—Blank Rome LLP

(57) ABSTRACT

The present invention relates to a novel VEGF protein product, and nucleic acid encoding the novel protein product, comprising exons 1–6 and 8 of the VEGF gene, and its use thereof in treating the cardiovascular system and its diseases through effects on anatomy, conduit function, and permeability. $VEGF_{145}$ has been found to be an active mitogen for vascular endothelial cells and to function as an angiogenic factor in-vivo. $VEGF_{145}$ has novel properties compared with previously characterized VEGF species with respect to cellular distribution, susceptibility to oxidative damage, and extra-cellular matrix (ECM) binding ability. The present invention provides methods of treating the cardiovascular system, enhancing endothelialization of diseased vessels, and enhancing drug permeation by providing the novel VEGF protein product. The invention also provides expression vectors, compositions, and kits for use in the methods of the invention.

5 Claims, 6 Drawing Sheets

ATGAACTTTCTGCTGTCTTGGGTGCATTGGAGCCTTGCCTTGCTGCTCTACCTCCACCATGCCAAGTG
GTCCCAGGCTGCACCCATGGCAGAAGGAGGGCAGAATCATCACGAAGTGGTGAAGTTCATGGAT
GTCTATCAGCGCAGCTACTGCCATCCAATCGAGACCCTGGTGGACATCTTCCAGGAGTACCCTGATGA
GATCGAGTACATCTTCAAGCCATCCTGTGTGCCCCTGATGCGATGCGGGGGCTGCTGCAATGACGAG
GGCCTGGAGTGTGTGCCCACTGAGGAGTCCAACATCACCATGCAGATTATGCGGATCAAACCTCACCA
AGGCCAGCACATAGGAGAGATGAGCTTCCTACAGCACAACAAATGTGAATGCAGACCAAAGAAAGATA
GAGCAAGACAAGAAAAAAAATCAGTTCGAGGAAAGGGAAAGGGGCAAAAAACGAAGCGCAAGAAATC
CCGGTATAAGTCCTGGAGCGTATGTGACAAGCCGAGGCGGTGA

FIG. 2

APMAEGGGQNHHEVVKFMDVYQRSYCHPIETLVDIFQEYPDEIEYIFKPSCVPLMRCGGCCNDEGLE
CVPTEESNITMQIMRIKPHQGQHIGEMSFLQHNKCECRPKKDRARQEKKSVRGKGKGQKRKRKKSRY
KSWSVCDKPRR

FIG. 3

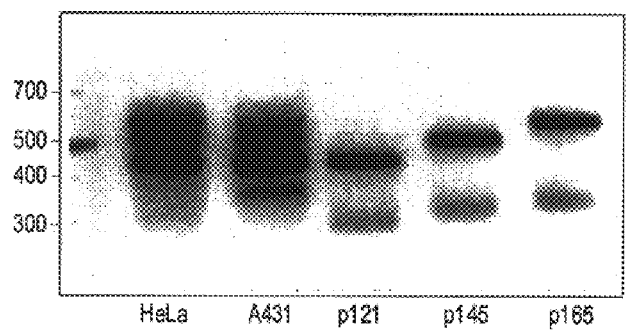

FIG. 5

SEQUENCE LISTING

<160> NUMBER OF SEQ ID NOS: 9

<210> SEQ ID NO 1
<211> LENGTH: 516
<212> TYPE: DNA
<213> ORGANISM: Homo sapiens

<400> SEQUENCE: 1

```
atgaactttc tgctgtcttg ggtgcattgg agccttgcct tgctgctcta cctccaccat      60
gccaagtggt cccaggctgc acccatggca gaaggaggag ggcagaatca tcacgaagtg     120
gtgaagttca tggatgtcta tcagcgcagc tactgccatc caatcgagac cctggtggac     180
atcttccagg agtaccctga tgagatcgag tacatcttca agccatcctg tgtgcccctg     240
atgcgatgcg gggctgctg caatgacgag ggcctggagt gtgtgcccac tgaggagtcc     300
aacatcacca tgcagattat gcggatcaaa cctcaccaag gccagcacat aggagagatg     360
agcttcctac agcacaacaa atgtgaatgc agaccaaaga aagatagagc aagacaagaa     420
aaaaaatcag ttcgaggaaa gggaaagggg caaaaacgaa agcgcaagaa atcccggtat     480
aagtcctgga gcgtatgtga caagccgagg cggtga                              516
```

<210> SEQ ID NO 2
<211> LENGTH: 145
<212> TYPE: PRT

<213> ORGANISM: Homo sapiens
<220> FEATURE:
<223> OTHER INFORMATION: coding sequence for VEGF 145

<400> SEQUENCE: 2

```
Ala Pro Met Ala Glu Gly Gly Gln Asn His His Glu Val Val Lys
 1               5                  10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Cys Asp Lys Pro Arg
    130                 135                 140

Arg
145
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
ggagagatga gcttcctaca g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
tcaccgcctt ggcttgtcac a                                              21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 5
gcttccggct cgtatgttgt gtgg                                           24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: primer -continued

```
<400> SEQUENCE: 6
acgctccagg acttataccg gga                                                  23

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
ggtaacgcca gggttttccc agtc                                                 24

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 8
cggtataagt cctggagcgt atgtgacaag ccgaggcggt ga                             42

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
gcagagctcg tttagtgaac                                                      20
```

ANGIOGENIC FACTOR AND USE THEREOF IN TREATING CARDIOVASCULAR DISEASE

This application is a divisional application of U.S. application Ser. No. 08/784,551, filed on Jan. 21, 1997, now issued U.S. Pat. No. 6,013,780, which claims priority to provisional U.S. Application No. 60/025,537, filed on Sep. 6, 1996.

BACKGROUND OF THE INVENTION

The present invention relates to the treatment of the cardiovascular system and its diseases through effects on anatomy, conduit function, and permeability, and more particularly to a method of treating cardiovascular disease by stimulating vascular cell proliferation using a growth factor thereby stimulating endothelial cell growth and vascular permeability.

Cardiovascular diseases are generally characterized by an impaired supply of blood to the heart or other target organs. Myocardial infarction (MI), commonly referred to as heart attacks, are a leading cause of mortality as 30% are fatal in the in the first months following the heart attack. Heart attacks result from narrowed or blocked coronary arteries in the heart which starves the heart of needed nutrients and oxygen. When the supply of blood to the heart is compromised, cells respond by generating compounds that induce the growth of new blood vessels so as to increase the supply of blood to the heart. These new blood vessels are called collateral blood vessels. The process by which new blood vessels are induced to grow out of the existing vasculature is termed angiogenesis, and the substances that are produced by cells to induce angiogenesis are the angiogenic factors.

Unfortunately, the body's natural angiogenic response is limited and often inadequate. For this reason, the discovery of angiogenic growth factors has lead to the emergence of an alternative therapeutic strategy which seeks to supplement the natural angiogenic response by supplying exogenous angiogenic substances.

Attempts have been made to stimulate angiogenesis by administering various growth factors. U.S. Pat. No. 5,318,957 to Cid et al. discloses a method of stimulating angiogenesis by administering haptoglobins (glyco-protein with two polypeptide chains linked by disulfide bonds). Intracoronary injection of a recombinant vector expressing human fibroblast growth factor-5 (FGF-5) (i.e., in vivo gene transfer) in an animal model resulted in successful amelioration of abnormalities in myocardial blood flow and function. (Giordano, F. J.,et. al. *Nature Med* 2, 534–539, 1996). Recombinant adenoviruses have also been used to express angiogenic growth factors in-vivo. These included acidic fibroblast growth factor (Muhlhauser, J., et. al. *Hum. Gene Ther.* 6, 1457–1465, 1995), and one of the VEGF forms, $VEGF_{165}$ (Muhlhauser, J., et. al. *Circ. Res.* 77, 1077–1086, 1995).

One of the responses of heart muscle cells to impaired blood supply involves activation of the gene encoding Vascular Endothelial Growth Factor ("VEGF") (Banai, S., et. al. *Cardiovasc. Res.* 28:1176–1179, 1994). VEGFs are a family of angiogenic factors that induce the growth of new collateral blood vessels. The VEGF family of growth factors are specific angiogenic growth factors that target endothelial (blood vessel-lining) cells almost exclusively. (Reviewed in Ferrara et al., *Endocr. Rev.* 13:18–32 (1992); Dvorak et al., *Am. J. Pathol.* 146:1029–39 (1995); Thomas, *J. Biol. Chem.* 271:603–06 (1996)). Expression of the VEGF gene is linked in space and time to events of physiological angiogenesis, and deletion of the VEGF gene by way of targeted gene disruption in mice leads to embryonic death because the blood vessels do not develop. It is therefore the only known angiogenic growth factor that appears to function as a specific physiological regulator of angiogenesis.

In vivo, VEGFs induce angiogenesis (Leung et al., *Science* 246:1306–09, 1989) and increase vascular permeability (Senger et al., *Science* 219:983–85, 1983). VEGFs are now known as important physiological regulators of capillary blood vessel formation. They are involved in the normal formation of new capillaries during organ growth, including fetal growth (Peters et al., *Proc. Natl. Acad. Sci. USA* 90:8915–19, 1993), tissue repair (Brown et al., *J. Exp. Med.* 176:1375–79, 1992), the menstrual cycle, and pregnancy (Jackson et al., *Placenta* 15:341–53, 1994; Cullinan & Koos, *Endocrinology* 133:829–37, 1993; Kamat et al., *Am. J. Pathol.* 146:157–65, 1995). During fetal development, VEGFs appear to play an essential role in the de novo formation of blood vessels from blood islands (Risau & Flamme, *Ann. Rev. Cell. Dev. Biol.* 11:73–92, 1995), as evidenced by abnormal blood vessel development and lethality in embryos lacking a single VEGF allele (Carmeliet et al., *Nature* 380:435–38, 1996). Moreover, VEGFs are implicated in the pathological blood vessel growth characteristic of many diseases, including solid tumors (Potgens et al., *Biol. Chem. Hoppe-Seyler* 376:57–70, 1995), retinopathies (Miller et al., *Am. J. Pathol.* 145:574–84, 1994; Aiello et al., *N. Engl. J. Med.* 331:1480–87, 1994; Adamis et al., *Am. J. Ophthalmol.* 118:445–50, 1994), psoriasis (Detmar et al., *J. Exp. Med.* 180:1141–46, 1994), and rheumatoid arthritis (Fava et al., *J. Exp. Med.* 180:341–46, 1994).

Using the rabbit chronic limb ischemia model, it has been shown that repeated intramuscular injection or a single intra-arterial bolus of VEGF can augment collateral blood vessel formation as evidenced by blood flow measurement in the ischemic hindlimb (Pu, et al., *Circulation* 88:208–15, 1993; Bauters et al., *Am. J. Physiol.* 267:H1263–71, 1994; Takeshita et al., *Circulation* 90 [part 2], II-228–34, 1994; Bauters et al., *J. Vasc. Surg.* 21:314–25, 1995; Bauters et al., *Circulation* 91:2802–09, 1995; Takeshita et al., *J. Clin. Invest.* 93:662–70, 1994). In this model, VEGF has also been shown to act synergistically with basic FGF to ameliorate ischemia (Asahara et al., *Circulation* 92:[suppl 2], II-365–71, 1995). VEGF was also reported to accelerate the repair of balloon-injured rat carotid artery endothelium while at the same time inhibiting pathological thickening of the underlying smooth muscle layers, thereby maintaining lumen diameter and blood flow (Asahara et al., *Circulation* 91:2793–2801, 1995). VEGF has also been shown to induce EDRF (Endothelin-Derived Relaxin Factor (nitric oxide))-dependent relaxation in canine coronary arteries, thus potentially contributing to increased blood flow to ischemic areas via a secondary mechanism not related to angiogenesis (Ku et al., *Am. J. Physiol.* 265:H586–H592, 1993).

Activation of the gene encoding VEGF results in the production of several different VEGF variants, or isoforms, produced by alternative splicing wherein the same chromosomal DNA yields different mRNA transcripts containing different exons thereby producing different proteins. Such variants have been disclosed, for example, in U.S. Pat. No. 5,194,596 to Tischer et al. which identifies human vascular endothelial cell growth factors having peptide sequence lengths of 121, and 165 amino acids (i.e., $VEGF_{121}$ and $VEGF_{165}$). Additionally, $VEGF_{189}$ and $VEGF_{206}$ have also been characterized and reported (Neufeld, G., et. al. *Cancer Metastasis Rev.* 15:153–158, 1996).

As depicted in FIG. 1, the domain encoded by exons 1–5 contains information required for the recognition of the known VEGF receptors KDR/flk-1 and flt-1 (Keyt, B. A., et. al. *J. Biol Chem* 271:5638–5646, 1996), and is present in all known VEGF isoforms. The amino-acids encoded by exon 8 are also present in all known isoforms. The isoforms may be distinguished however by the presence or absence of the peptides encoded by exons 6 and 7 of the VEGF gene, and the presence or absence of the peptides encoded by these exons results in structural differences which are translated into functional differences between the VEGF forms (reviewed in: Neufeld, G., et. al. *Cancer Metastasis Rev.* 15, 153–158, 1996).

Exon 6 can terminate after 72 bp at a donor splice site wherein it contributes 24 amino acids to VEGF forms that contain it such as $VEGF_{189}$. This exon 6 form is referred to as exon 6a. However, the VEGF RNA can be spliced at the 3' end of exon 6 using an alternative splice site located 51 bp downstream to the first resulting in a larger exon 6 product containing 41 amino-acids. The additional 17 amino-acids added to the exon 6 product as a result of this alternative splicing are referred to herein as exon 6b. $VEGF_{206}$ contains the elongated exon 6 composed of 6a and 6b, but this VEGF form is much rarer than $VEGF_{189}$. (Tischer, E., et al., *J. Biol. Chem.* 266, 11947–11954; Houck, K. A., et al., *Mol. Endocrinol.*, 12, 1806–1814, 1991).

A putative fifth form of VEGF, $VEGF_{145}$, has been noted in the human endometrium, using PCR. The authors state that the sequence of the cDNA of the $VEGF_{145}$ splice variant indicated that it contained exons 1–5, 6 and 8. However, it is uncertain whether the authors found that the splice variant contained exons 6a and 6b as in $VEGF_{206}$, exon 6a as in $VEGF_{189}$, or exon 6b. The authors state that since the splice variant retains exon 6 it is probable that it will be retained by the cell as are the other members of the family that contain this exon. (Charnock-Jones et al., *Biology of Reproduction* 48, 1120–1128 (1993). See also, Bacic M, et al. *Growth Factors* 12, 11–15, 1995). The biologic activity of this form has not heretofore been established. (Cheung, C. Y., et al., *Am J. Obstet Gynecol.*, 173, 753–759, 1995); Anthony, F. W. et al., *Placenta*, 15, 557–561, 1994). The various isoforms, and the exons that encode the isoforms, are depicted in FIG. 1.

The four known forms of VEGF arise from alternative splicing of up to eight exons of the VEGF gene ($VEGF_{121}$, exons 1–5,8; $VEGF_{165}$, exons 1–5,7,8; $VEGF_{189}$, exons 1–5, 6a, 7, 8; $VEGF_{206}$, exons 1–5, 6a, 6b, 7, 8 (exon 6a and 6b refer to 2 alternatively spliced forms of the same exon)) (Houck et al., *Mol. Endocr.*, 5:1806–14 (1991)). All VEGF genes encode signal peptides that direct the protein into the secretory pathway. For example, $VEGF_{165}$ cDNA encodes a 191-residue amino acid sequence consisting of a 26-residue secretory signal peptide sequence, which is cleaved upon secretion of the protein from cells, and the 165-residue mature protein subunit. However, only $VEGF_{121}$ and $VEGF_{165}$ are found to be readily secreted by cultured cells whereas $VEGF_{189}$ and $VEGF_{206}$ remain associated with the producing cells. These VEGF forms possess an additional highly basic sequence encoded by exon 6 corresponding to residues 115–139 in $VEGF_{189}$ and residues 115–156 in $VEGF_{206}$. These additions confer a high affinity to heparin and an ability to associate with the extracellular matrix (matrix-targeting sequence) (Houck, K. A. et al., *J. Biol. Chem.* 267:26031–37 (1992) and Thomas, *J. Biol. Chem.* 271:603–06 (1996)). The mitogenic activities of $VEGF_{121}$ and $VEGF_{165}$ are similar according to the results of several groups (Neufeld, G., et al., *Cancer Metastasis Rev.* 15:153–158 (1996) although one research group has shown evidence indicating that $VEGF_{121}$ is significantly less active (Keyt, B. A., et al.,*J. Biol. Chem.* 271:7788–7795 (1996). It is unclear whether the two longer VEGF forms, $VEGF_{189}$ and $VEGF_{206}$, are as active or less active than the two shorter forms since it has not been possible to obtain them in pure form suitable for quantitative measurements. This failure is due in part to their strong association with producing cells and extracellular matrices which is impaired by the presence of exon-6 derived sequences apparently acting in synergism with exon-7 derived sequences groups (Neufeld, G., et al., *Cancer Metastasis Rev.* 15:153–158 (1996).

As described in more detail herein, each of the VEGF splice variants that have heretofore been characterized have one or more of the following disadvantages with respect to stimulating angiogenesis of endothelial cells in the treatment of cardiovascular diseases: (i) failure to bind to the extra-cellular matrix (ECM) resulting in faster clearance and a shorter period of activity, (ii) failure to secrete into the medium (i.e. remaining cell-associated) so as to avoid reaching and acting on the endothelial cells, and (iii) susceptibility to oxidative damage thereby resulting in shorter half-life.

Accordingly, there is a need for a new form of VEGF that avoids the aforementioned disadvantages and that can be usefully applied in stimulating angiogenesis in cardiovascular disease patients would be most desirable.

SUMMARY OF THE INVENTION

The present invention relates to a novel VEGF protein product, and a nucleic acid encoding the novel protein product comprising exons 1–6a and 8 of the VEGF gene, (hereinafter "$VEGF_{145}$") and the use thereof in treating the cardiovascular system and its diseases through effects on anatomy, conduit function, and permeability. $VEGF_{145}$ has been found to be an active mitogen for vascular endothelial cells and to function as an angiogenic factor in-vivo. $VEGF_{145}$ was favorably compared with previously characterized VEGF species with respect to cellular distribution, susceptibility to oxidative damage, and extra-cellular matrix (ECM) binding ability.

Previous research relating to the binding affinities of the various VEGF isoforms found that $VEGF_{165}$, which lacks exon 6, binds relatively weakly to heparin and also binds very weakly to the extracellular matrix, (Park, J. E., et al., *Mol. Biol. Cell* 4:1317–1326 (1993). $VEGF_{145}$, which binds as weakly as $VEGF_{165}$ to heparin, binds much better than $VEGF_{165}$ to the extracellular matrix. However, unlike $VEGF_{189}$, $VEGF_{145}$ is secreted from producer cells and binds efficiently to the ECM. This combination of properties render $VEGF_{145}$ the only known VEGF variant that is secreted from producing cells retaining at the same time extracellular matrix binding properties. Hence, it will likely diffuse towards the target blood vessels, while some of the produced $VEGF_{145}$ will be retained by extracellular matrix components along the path of diffusion. This ECM bound pool will dissociate slowly allowing a longer period of activity. Furthermore, the biological activity of $VEGF_{145}$ is protected against oxidative damage unlike VEGF forms such as $VEGF_{121}$ thereby giving it a longer half-life.

In sum, $VEGF_{145}$ clearly possesses a unique combination of biological properties that distinguish it from the other VEGF forms. This unique combination of properties of $VEGF_{145}$ renders it a preferred therapeutic agent for the treatment of the cardiovascular system and its diseases as well as other diseases characterized by vascular cell proliferation. In particular, the cDNA may be employed in gene therapy for treating the cardiovascular system and its diseases.

Endothelial cell proliferation, such as that which occurs in angiogenesis, is also useful in preventing restenosis following balloon angioplasty. The balloon angioplasty procedure often injuries the endothelial cells lining the inner walls of blood vessels. Smooth muscle cells often infiltrate into the opened blood vessels causing a secondary obstruction in a process known as restenosis. The proliferation of the endothelial cells located at the periphery of the balloon-induced damaged area in order to cover the luminal surface of the vessel with a new monolayer of endothelial cells would potentially restore the original structure of the blood vessel.

Thus, the present invention provides a method of treating cardiovascular disease in a mammal comprising the step of transfecting cells of said mammal with a polynucleotide which encodes $VEGF_{145}$. In preferred aspects, the polynucleotide is cloned into a vector. In further preferred aspects, the vector is an adenovirus vector. The adenovirus vector is preferably delivered to the mammal by injection; preferably, about $10^{10}$ to about $10^{14}$ adenovirus vector particles are delivered in the injection. More preferably, about $10^{11}$ to about $10^{13}$ adenovirus vector particles are delivered in the injection. Most preferably, about $10^{12}$ adenovirus vector particles are delivered in the injection.

In further preferred aspects, the polynucleotide which encodes $VEGF_{145}$ is delivered to the heart of a mammal. The delivery of the polynucleotide is preferably by intracoronary injection into one or both arteries, preferably according to the methods set forth in PCT/US96/02631, published Sep. 6, 1996 as WO96/26742, hereby incorporated by reference herein. Preferably, the intracoronary injection is conducted about 1 cm into the lumens of the left and right coronary arteries.

In other preferred aspects of the invention, the cells of the mammal are transfected in vivo. In other preferred aspects, the cells are transfected ex vivo.

In yet other preferred aspects of the invention, the polynucleotide may be introduced into the mammal through a catheter.

In one embodiment of the invention, the polynucleotide which encodes $VEGF_{145}$ comprises a base sequence as defined in the Sequence Listing by SEQ ID No. 1. In preferred embodiments, the polynucleotide sequence encoding $VEGF_{145}$ is present in an expression vector. Thus, in a preferred aspect of the invention, the invention provides an expression vector comprising a polynucleotide sequence encoding $VEGF_{145}$ species, said species being selected from the group consisting of:

(a) $VEFG_{145}$;
(b) a biologically active fragment of $VEGF_{145}$; and
(c) a biologically active derivative of $VEGF_{145}$, wherein an amino acid residue has been inserted, substituted or deleted in or from the amino acid sequence of the $VEGF_{145}$ or its fragment. In preferred aspects, the polynucleotide encodes $VEGF_{145}$. In more preferred aspects, the polynucleotide comprises a base sequence as defined in the Sequence Listing by SEQ ID No. 1.

In a preferred embodiment of the invention, the polynucleotide encoding $VEGF_{145}$ is present in an adenovirus expression vector, thus, in preferred aspects, the polynucleotide is flanked by adenovirus sequences. In yet other preferred aspects, the polynucleotide sequence is operably linked at its 5' end to a promoter sequence that is active in vascular endothelial cells. In preferred expression vectors, the expression vector further comprises a partial adenoviral sequence from which the EIA/EIB genes have been deleted.

Also provided in the present invention are kits for intracoronary injection of a recombinant vector expressing $VEGF_{145}$ comprising:

a polynucleotide encoding $VEGF_{145}$ cloned into a vector suitable for expression of said polynucleotide in vivo, a suitable container for said vector, and instructions for injecting said vector into a patient. In more preferred aspects, the polynucleotide is cloned into an adenovirus expression vector.

In other preferred embodiments of the invention, the methods, compositions, and vectors of the present invention may be used to treat cardiovascular disease in a mammal comprising the step of administering to said mammal $VEGF_{145}$ in a therapeutically effective amount to stimulate angiogenesis. In other preferred embodiments, the methods, compositions, and vectors of the present invention may be used to treat vascular disease in a mammal comprising the step of administering to said mammal $VEGF_{145}$ in a therapeutically effective amount to stimulate vascular cell proliferation. In yet other preferred embodiments of the present invention, the methods, compositions, and vectors of the invention may be used to enhance endothelialization of diseased vessels comprising the step of administering to a mammal a therapeutically effective amount of $VEGF_{145}$. Preferably, endothelialization comprises reendothelialization after angioplasty, to reduce or prevent restenosis. Those of skill in the art will recognize that patients treated according to the methods of the present invention may be treated with or without a stent.

In yet other preferred embodiments of the present invention, the methods, compositions, and vectors of the invention may be used to enhance drug permeation by tumors comprising administering to a patient a nucleic acid molecule coding for $VEGF_{145}$. The $VEGF_{145}$ may be delivered directly to a tumor cell, or it may be delivered into the vascular system, preferably at a site located close to the site of the tumor. Thus, delivery of $VEGF_{145}$ in conjunction with chemotherapy to remove or reduce the size of a tumor, will help to enhance the effectiveness of the chemotherapy by increasing drug uptake by the tumor. The $VEGF_{145}$ delivered in this method may either be through direct delivery of the polypeptide or protein, or through gene therapy.

In another embodiment of the invention is provided a therapeutic composition comprising a pharmaceutically acceptable carrier and $VEGF_{145}$ in a therapeutically effective amount to stimulate vascular cell proliferation.

In other preferred embodiments of the invention is provided a filtered injectable adenovirus vector preparation, comprising: a recombinant adenoviral vector, said vector containing no wild-type virus and comprising:

a partial adenoviral sequence from which the E1A/E1B genes have been deleted, and a transgene coding for a $VEGF_{145}$, driven by a promoter flanked by the partial adenoviral sequence; and a pharmaceutically acceptable carrier.

In other preferred aspects, the invention provides a recombinant plasmid comprising a polynucleotide which codes for $VEGF_{145}$. In yet other preferred aspects, the invention provides a transformed microorganism transformed with the recombinant plasmid.

With the foregoing and other objects, advantages and features of the invention that will become hereinafter apparent, the nature of the invention may be more clearly understood by reference to the following detailed description of the invention, the figures, and the appended claims.

BRIEF DESCRIPTION OF THE DRAWINGS

FIG. 2 is a nucleotide sequence of $VEGF_{145}$ cDNA protein coding region [SEQ ID No. 1]. Underlined is the sequence coding for a signal sequence for secretion that is cleaved off the mature protein.

FIG. 3 is the amino acid protein sequence of a mature $VEGF_{145}$ monomer [SEQ. ID. No. 2].

FIG. 5 is a photograph showing the binding of $VEGF_{145}$ mRNA as seen in a reverse PCR type experiment analyzing mRNA isolated from two-cancerous cell lines derived from the female reproductive system (HeLa and A431 cells). Total RNA from HeLa and A431 cells was translated into cDNA and amplified by PCR using radioactively labeled nucleotides as described in materials and methods. Plasmids containing the $VEGF_{121}$ cDNA, the $VEGF_{165}$ cDNA, and the $VEGF_{145}$ recombinant cDNA were included in separate PCR reactions using the primers described in materials and methods. Shown is an autoradiogram of the gel.

a. ECM-coated 96 well dishes were incubated with increasing concentrations of $VEGF_{145}$ (■) or $VEGF_{165}$ ( ). The amount of ECM-bound VEGF was quantified using the M-35 anti-VEGF monoclonal antibody as described in materials and methods.

b. $^{125}I$-$VEGF_{145}$ (Lanes 1 and 2, 30 ng/ml or $^{125}I$-$VEGF_{165}$ (Lane 3, 50 ng/ml) was bound to ECM coated wells. Heparin (10 μg/ml) was added with the $VEGF_{145}$ in Lane 2. The binding and the subsequent extraction of bound growth factors were done as described in materials and methods. Extracted growth factors were subjected to SDS/PAGE (12% gel) followed by autoradiography.

c. The $^{125}I$-$VEGF_{145}$ used in the experiment shown in panel B (0.2 ng) was chromatographed under reducing conditions on a 12% SDS/PAGE gel. Shown is an autoradiogram of the gel.

FIGS. 9(A–B) is a description of an experiment showing the effects of heparinase digestion of an ECM produced by bovine corneal endothelial cells on the binding of $VEGF_{145}$ and bFGF to the ECM.

a. Effect of heparin and heparinase on growth factor binding: ECM coated wells were incubated with or without 0.1 u/ml heparinase-II in binding buffer for 2 h at 37° C. Subsequently, $^{125}I$-$VEGF_{145}$ (40 ng/ml) or $^{125}I$-bFGF (114 ng/ml) were added to the wells in the presence or absence of 10 μg/ml heparin. Following incubation for 3 h at 25° C., the wells were washed and ECM-associated iodinated growth factors were dissociated by digestion with trypsin for 15 min at 37° C. The amount of bound growth factor was determined using a gamma-counter (100% binding was 15,000 and 25,000 CPM/well for $^{125}I$-$VEGF_{145}$ and $^{125}I$-FGF respectively).

b. Effect of heparin and heparinase-II on the release of bound growth factors from the ECM. $^{125}I$-$VEGF_{145}$ or $^{125}I$-bFGF were bound to ECM-coated wells as described above. The wells were washed and re-incubated in binding buffer alone, with 10 μg/ml heparin, or with 0.1 U/ml heparinase-II in a final volume of 50 μl. Following 12 h of incubation at 25° C., the integrity of the ECM was verified by microscopy, and 45 μl aliquots were taken for counting in a gamma-counter. NaOH was then added to the wells and the amount of ECM-associated growth factors determined. The experiment was carried out in parallel to the experiment described in panel A above. The experiments in panels A and B were carried out in duplicates and variation did not exceed 10%. Shown are the mean values. The experiments were repeated 4 times with similar results.

Figure 10:
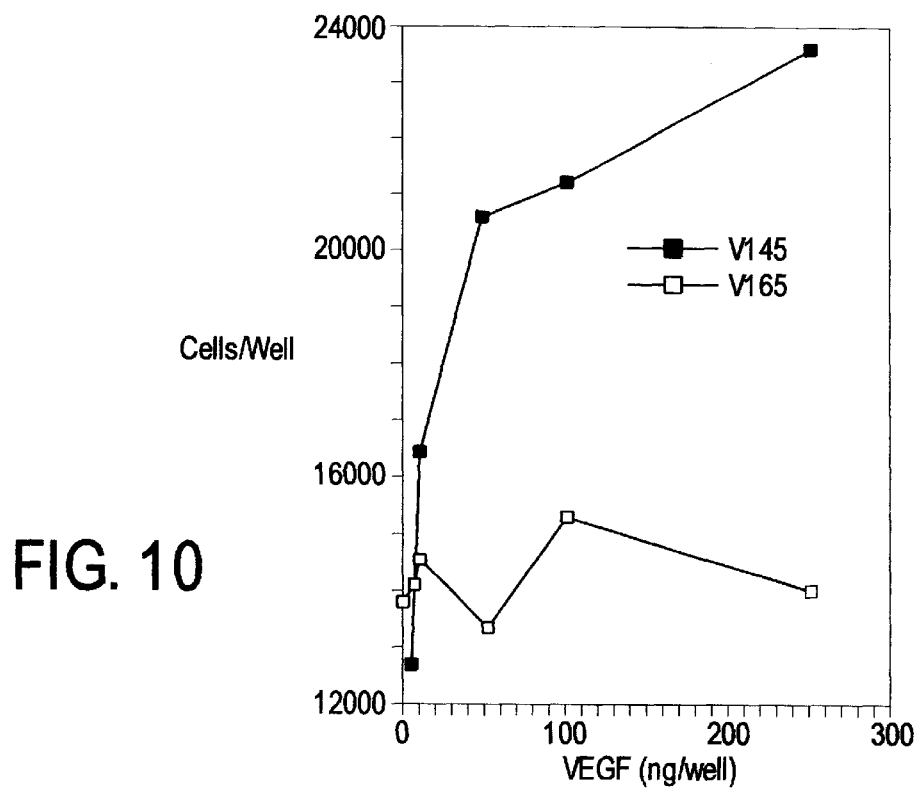

FIG. 10 is a graph showing that $VEGF_{145}$ bound to the ECM is biologically active. Wells of 24 well dishes were coated with an ECM produced by BCE cells cultured in the presence of 30 nM chlorate. The ECM coated wells were incubated with increasing concentrations of $VEGF_{145}$ (■) or $VEGF_{165}$ as indicated, and washed extensively as described. HUVEC cells (15,000 cells/well) were seeded in the ECM coated wells in growth medium lacking growth factors. Cells were trypsinzed and counted after three days. The numbers represent the average number of cells in duplicate wells.

Figure 11:
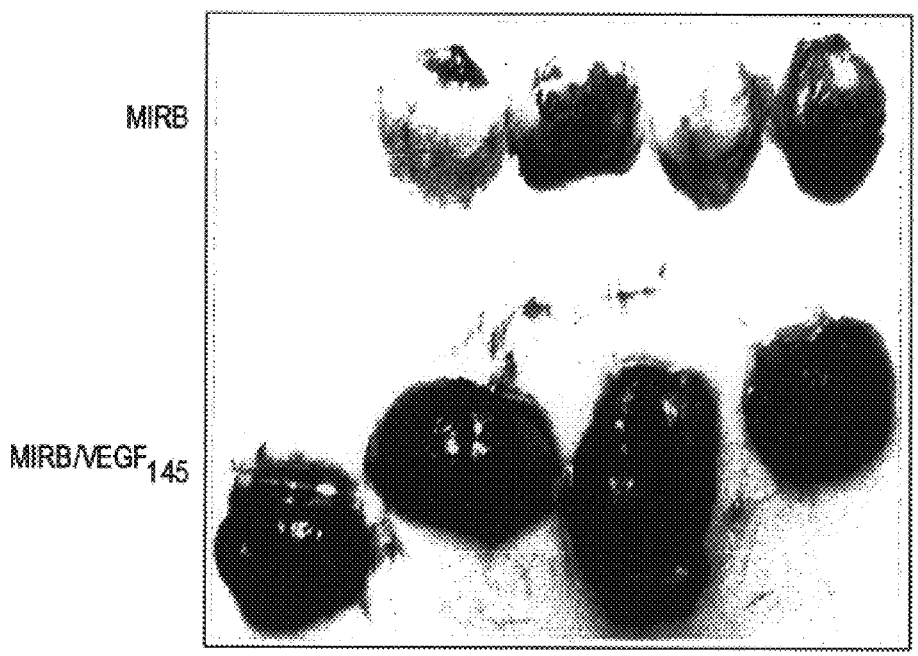

FIG. 11 is a photograph showing clusters of alginate beads containing cells expressing or not expressing $VEGF_{145}$. Clusters containing $VEGF_{145}$ expressing cells are gorged with blood. $VEGF_{145}$ stimulates angiogenesis in vivo: The angiogenic activity of $VEGF_{145}$ was determined using the alginate assay. Stable clones of BHK-21 cells transfected with the MIRB expression vector (MIRB) or with the VEGF$_{145}$ expression vector MIRB/VEGF$_{145}$, were trypsinized and suspended in DMEM to a concentration of 2.7×10$^7$ cells/ml. Sodium alginate (1.2%, 0.66 ml) was mixed with 1.33 mil of cell suspension. Beads of 1 μl diameter were formed by contact with a solution of 80 mM CaCl$_2$. The beads were washed three times with saline. Each Balb/c mouse out of a group of 4 was injected subcutaneously with 400 μl of packed beads containing a given cell type. Clusters of beads were excised after 4 days and photographed. Blood-rich areas appear as dark areas in the photograph.

DETAILED DESCRIPTION OF THE INVENTION

The following abbreviations are used herein.

| | |
|---|---|
| BCE | Bovine corneal endothelial cells |
| bFGF | Basic fibroblast growth factor |
| ECM | Extracellular matrix |
| HUVEC | Human umbilical vein derived endothelial cells |
| VEGF | Vascular endothelial growth factor |
| VEGF$_{xxx}$ | Vascular endothelial growth factor form containing a designated number (xxx) of amino-acids. |

The present invention relates to a novel VEGF protein product, and nucleic acids encoding the novel protein product (FIG. 2), comprising exons 1–6 and 8 of the VEGF gene, and its use thereof in treating cardiovascular disease. As used herein "cardiovascular disease" means disease which results from a cardiovascular insufficiency, including, but not limited to, coronary artery disease, congestive heart failure, and peripheral vascular disease. The methods of the present invention relate to the treatment of mammalian patients, preferably humans.

The VEGF$_{145}$ protein forms active homodimers bound by disulfide bridges (FIG. 3). VEGF$_{145}$ is an active mitogen for vascular dendothelial cells and to function as an angiogenic factor in-vivo. VEGF$_{145}$ was compared with previously characterized VEGF species with respect to cellular distribution, susceptibility to oxidative damage, and extracellular matrix (ECM) binding ability. VEGF$_{145}$ is secreted from producer cells and can bine efficiently to the ECM, rendering it the only known VEGF variant having both of these attributes.

As used herein, "vascular endothelial cell growth factor," or "VEGF" refers to a family of angiogenic growth factors encoded by the human VEGF gene.

"VEGF$_{145}$" refers to a VEGF form containing about 145 amino-acids created as a result of alternative splicing of VEGF mRNA and containing the peptides encoded by exons 1–5, 6a and 8 of the VEGF gene. The term "VEGF$_{145}$" also refers to derivatives and functional equivalents of the native VEGF$_{145}$ nucleic acid or amino acid sequence. Mature VEGF$_{145}$ monomers comprise the amino acid sequence shown in FIG. 3. However, as used herein, the term VEGF$_{145}$ refers to both the mature form and the pro-form of VEGF$_{145}$, including a signal sequence, or derivatives or functional equivalents thereof. VEGF$_{145}$ is expressed in several cell lines (FIG. 4) and was shown to be expressed in OC238 ovarian carcinoma cells using sequencing of the region encompassing exons 5–8 of VEGF cDNA prepared from the OC238 cells.

"Derivatives" of a VEGF$_{145}$ polypeptide or subunit are functional equivalents having similar amino acid sequence and retaining, to some extent, the activities of VEGF$_{145}$. By "functional equivalent" is meant the derivative has an activity that can be substituted for the activity of VEGF$_{145}$. Preferred functional equivalents retain the full level of activity of VEGF$_{145}$ as measured by assays known to these skilled in the art, and/or in the assays described herein. Preferred functional equivalents have activities that are within 1% to 10,000% of the activity of VEGF$_{145}$, more preferably between 10% to 1000%, and more preferably within 50% to 200%. Derivatives have at least 50% sequence similarity, preferably 70%, more preferably 90%, and even more preferably 95% sequence similarity to VEGF$_{145}$. "Sequence similarity" refers to "homology" observed between amino acid sequences in two different polypeptides, irrespective of polypeptide origin.

The ability of the derivative to retain some activity can be measured using techniques described herein and/or using techniques known to those skilled in the art for measuring the activity of other VEGF isoforms. Derivatives include modification occurring during or after translation, for example, by phosphorylation, glycosylation, crosslinking, acylation, proteolytic cleavage, linkage to an antibody molecule, membrane molecule or other ligand (see Ferguson et al., 1988, Annu. Rev. Biochem. 57:285–320).

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

Although the effect of an amino acid change varies depending upon factors such as phosphorylation, glycosylation, intra-chain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as amino acids of the formula $H_2N(CH_2)_nCOOH$ where n is 2–6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and non-polar amino acids such as cyclohexyl alanine (Cha); altered acidic amino acids such as cysteic acid (Cya); and altered basic amino acids such as ornithine (Orn).

Preferred derivatives have one or more amino acid alteration(s) that do not significantly affect the receptor-binding activity of $VEGF_{145}$. In regions of the $VEGF_{145}$ polypeptide sequence not necessary for $VEGF_{145}$ activity, amino acids may be deleted, added or substituted with less risk of affecting activity. In regions required for $VEGF_{145}$ activity, amino acid alterations are less preferred as there is a greater risk of affecting $VEGF_{145}$ activity. Such alterations should be conservative alterations. For example, one or more amino acid residues within the sequence can be substituted by another amino acid of a similar polarity which acts as a functional equivalent.

Conserved regions tend to be more important for protein activity than non-conserved regions. Standard procedures can be used to determine the conserved and non-conserved regions important for receptor activity using in vitro mutagenesis techniques or deletion analyses and measuring receptor activity as described by the present disclosure.

Derivatives can be produced using standard chemical techniques and recombinant nucleic acid molecule techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Sambrook et al., *Molecular Cloning,* Cold Spring Harbor Laboratory Press (1989). For example, Chapter 15 of Sambrook describes procedures for site-directed mutagenesis of cloned DNA.

In one aspect the invention features a nucleic acid molecule, or poly nucleotide encoding $VEGF_{145}$. In some situations it is desirable for such nucleic acid molecule to be enriched or purified. By the use of the term "enriched" in reference to nucleic acid molecule is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased. The term significant here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

The nucleic acid molecule may be constructed from an existing VEGF nucleotide sequence by modification using, for example, oligonucleotide site-directed mutagenesis, or by deleting sequences using restriction enzymes, or as described herein. Standard recombinant techniques for mutagenesis such as in vitro site-directed mutagenesis (Hutchinson et al., *J. Biol. Chem.* 253:6551, (1978), Sambrook et al., Chapter 15, supra), use of TAB® linkers (Pharmacia), and PCR-directed mutagenesis can be used to create such mutations. The nucleic acid molecule may also be synthesized by the triester method or by using an automated DNA synthesizer.

The invention also features recombinant DNA vectors preferably in a cell or an organism. The recombinant DNA vectors may contain a sequence coding for $VEGF_{145}$ protein or a functional derivative thereof in a vector containing a promoter effective to initiate transcription in a host cell. The recombinant DNA vector may contain a transcriptional initiation region functional in a cell and a transcriptional termination region functional in a cell. Where the DNA vector contains sufficient control sequences, such as initiation and/or termination regions, such that the inserted nucleic acid molecule may be expressed in a host cell, the vector may also be called an "expression vector."

The present invention also relates to a cell or organism that contains the above-described nucleic acid molecule or recombinant DNA vector and thereby is capable of expressing a $VEGF_{145}$ peptide. The peptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

For example, the entire coding sequence of $VEGF_{145}$ may be combined with one or more of the following in an appropriate expression vector to allow for such expression: (1) an exogenous promoter sequence (2) a ribosome binding site (3) a polyadenylation signal (4) a secretion signal. Modifications can be made in the 5'-untranslated and 3'-untranslated sequences to improve expression in a prokaryotic or eukaryotic cell; or codons may be modified such that while they encode an identical amino acid, that codon may be a preferred codon in the chosen expression system. The use of such preferred codons is described in, for example, Grantham et al., *Nuc. Acids Res.,* 9:43–74 (1981), and Lathe, *J. Mol. Biol.,* 183:1–12 (1985) hereby incorporated by reference herein in their entirety.

If desired, the non-coding region 3' to the genomic VEGF$_{145}$ protein sequence may be operably linked to the nucleic acid molecule encoding VEGF$_{145}$. This region may be used in the recombinant DNA vector for its transcriptional termination regulatory sequences, such as termination and polyadenylation. Thus, by retaining the 3'-region naturally contiguous to the DNA sequence encoding VEGF, the transcriptional termination signals may be provided. Alternatively, a 3' region functional in the host cell may be substituted.

An operable linkage is a linkage in which the regulatory DNA sequences and the DNA sequence sought to be expressed are connected in such a way as to permit gene sequence expression. Two DNA sequences (such as a promoter region sequence and a VEGF145 protein sequence) are said to be operably linked if the nature of the linkage between the two DNA sequences does not (1) result in the introduction of a frame-shift mutation in the coding sequence, (2) interfere with the ability of the promoter region sequence to direct the transcription of VEGF145 PROTEIN gene sequence, or (3) interfere with the ability of the VEGF145 PROTEIN gene sequence to be transcribed by the promoter region sequence. Thus, a promoter region would be operably linked to a DNA sequence if the promoter were capable of effecting transcription of that DNA sequence. Thus, to express a VEGF$_{145}$ transcriptional and translational signals recognized by an appropriate host are necessary.

Those skilled in the art will recognize that the VEGF$_{145}$ protein of the present invention may also be expressed in various cell systems, both prokaryotic and eukaryotic, all of which are within the scope of the present invention.

Although the VEGF$_{145}$ protein of the present invention may be expressed in prokaryotic cells, which are generally very efficient and convenient for the production of recombinant proteins, the VEGF$_{145}$ produced by such cells will not be glycosylated and therefore may have a shorter half-life in vivo. Prokaryotes most frequently are represented by various strains of *E. coli*. However, other microbial strains may also be used, including other bacterial strains. Recognized prokaryotic hosts include bacteria such as *E. coli*, Bacillus, Streptomyces, Pseudomonas, Salmonella, Serratia, and the like. The prokaryotic host must be compatible with the replicon and control sequences in the expression plasmid.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include γgt10, γgt11 and the like; and suitable virus vectors may include pMAM-neo, pKRC and the like. Preferably, the selected vector of the present invention has the capacity to replicate in the selected host cell.

To express VEGF$_{145}$ polypeptides or subunits (or a functional derivative thereof) in a prokaryotic cell, it is necessary to operably link the VEGF$_{145}$ protein sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ (P$_L$ and P$_R$), the trp, recA, λacZ, λacI, and gal promoters of *E. coli*, the α-amylase (Ulmanen et al., *J. Bacteriol.* 162:176–182(1985)) and the ζ-28-specific promoters of *B. subtilis* (Gilman et at., *Gene sequence* 32:11–20(1984)), the promoters of the bacteriophages of Bacillus (Gryczan, *In: The Molecular Biology of the Bacilli, Academic Press, Inc.*, NY (1982)), and Streptomyces promoters (Ward et at., *Mol. Gen. Genet.* 203:468–478 (1986)). Prokaryotic promoters are reviewed by Glick (*J. Ind. Microbiot.* 1:277–282(1987)); Cenatiempo (*Biochimie* 68:505–516(1986)); and Gottesman (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404(1981)). The ribosome binding site and other sequences required for translation initiation are operably linked to the nucleic acid molecule coding for VEGF$_{145}$ by, for example, in frame ligation of synthetic oligonucleotides that contain such control sequences. For expression in prokaryotic cells, no signal peptide sequence is required. The selection of control sequences, expression vectors, transformation methods, and the like, are dependent on the type of host cell used to express the gene.

As used herein, "cell", "cell line", and "cell culture" may be used interchangeably and all such designations include progeny. Thus, the words "transformants" or "transformed cells" include the primary subject cell and cultures derived therefrom, without regard to the number of transfers. VEGF$_{145}$ expressed in prokaryotic cells is expected to comprise a mixture of properly initiated VEGF$_{145}$ protein peptides with the N-terminal sequence predicted from the sequence of the expression vector, and VEGF$_{145}$ protein peptides that have an N-terminal methionine resulting from inefficient cleaving of the initiation methionine during bacterial expression. Both types of VEGF$_{145}$ peptides are considered to be within the scope of the present invention as the presence of an N-terminal methionine is not expected to affect biological activity. It is also understood that all progeny may not be precisely identical in DNA content, due to deliberate or inadvertent mutations. However, as defined, mutant progeny have the same functionality as that of the originally transformed cell.

Preferred prokaryotic vectors include plasmids such as those capable of replication in *E. coil* (such as, for example, pBR322, ColE1, pSC101, pACYC 184, πVX. Such plasmids are, for example, disclosed by Sambrook (cf. "*Molecular Cloning: A Laboratory Manual*", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (*In: The Molecular Biology of the Bacilli*, Academic Press, NY (1982), pp. 307–329). Suitable Streptomyces plasmids include p1J101 (Kendall et al., *J. Bacteriol.* 169:4177–4183 (1987)), and streptomyces bacteriophages such as φC31 (Chater et al., *In: Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742(1978)).

Eukaryotic host cells that may be used in the expression systems of the present invention are not strictly limited, provided that they are suitable for use in the expression of VEGF$_{145}$ Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives.

The VEGF$_{145}$ proteins of the present invention may also be expressed in human cells such as human embryo kidney 293EBNA cells, which express Epstein-Barr virus nuclear antigen 1, as described, for example, in Olofsson, B. et al., *Proc. Natl. Acad. Sci.* USA 93:2576–2581 (1996). The cells are transfected with the expression vectors by using calcium phosphate precipitation, and the cells are then incubated for at least 48 hours. The VEGF$_{145}$ peptides may then be purified from the supernatant as described in Example 3.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the Drosophila larvae. Using insect cells as hosts, the Drosophila alcohol dehydrogenase promoter can be used. Rubin, *Science* 240:1453–1459(1988).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of VEGF$_{145}$ peptides.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of VEGF$_{145}$ in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288(1982)); the TK promoter of Herpes virus (McKnight, *Cell* 31:355–365 (1982)); the SV40 early promoter (Benoist et al., *Nature* (London) 290:304–310(1981)); the yeast gal4 gene sequence promoter (Johnston et al., *Proc. Natl. Acad Sci.* (USA) 79:6971–6975(1982); Silver et al., *Proc. Natl. Acad. Sci.* (USA) 81:5951–5955 (1984)).

Translation of eukaryotic mRNA is initiated at the codon which encodes the first methionine. For this reason, it is preferable to ensure that the linkage between a eukaryotic promoter and a DNA sequence that encodes a VEGF$_{145}$ (or a functional derivative thereof) does not contain any intervening codons which are capable of encoding a methionine (i.e., AUG). The presence of such codons results either in a formation of a fusion protein (if the AUG codon is in the same reading frame as the VEGF$_{145}$ protein coding sequence) or a frame-shift mutation (if the AUG codon is not in the same reading frame as the VEGF$_{145}$ protein coding sequence).

A VEGF$_{145}$ nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Because such molecules are incapable of autonomous replication, the expression of the gene may occur through the transient expression of the introduced sequence. Alternatively, permanent expression may occur through the integration of the introduced DNA sequence into the host chromosome.

A vector may be employed that is capable of integrating the desired gene sequences into the host cell chromosome. Cells that have stably integrated the introduced DNA into their chromosomes can be selected by also introducing one or more markers that allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Molec. Cell. Biol.* 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265–274(1982); Broach, In: "*The Molecular Biology of the Yeast Saccharomyces: Life Cycle and Inheritance*", Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, lipofection, calcium phosphate precipitation, direct microinjection, DEAE-dextran transfection, and the like. The most effective method for transfection of eukaryotic cell lines with plasmid DNA varies with the given cell type. After the introduction of the vector, recipient cells are grown in a selective medium, which selects for the growth of vector-containing cells. Expression of the cloned gene molecule(s) results in the production of $VEGF_{145}$. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

Production of the stable transfectants, may be accomplished by, for example, by transfection of an appropriate cell line with a eukaryotic expression vector, such as pCEP4, in which the coding sequence for $VEGF_{145}$ has been cloned into the multiple cloning site. These expression vectors contain a promoter region, such as the human cytomegalovirus promoter (CMV), that drive high-level transcription of desired DNA molecules in a variety of mammalian cells. In addition, these vectors contain genes for the selection of cells that stably express the DNA molecule of interest. The selectable marker in the pCEP4 vector encodes an enzyme that confers resistance to hygromycin, a metabolic inhibitor that is added to the culture to kill the nontransfected cells.

Cells that have stably incorporated the transfected DNA may be identified by their resistance to selection media, as described above, and clonal cell lines will be produced by expansion of resistant colonies. The expression of $VEGF_{145}$ by these cell lines may be assessed by methods known in the art, for example, by solution hybridization and Northern blot analysis.

Pharmaceutical Compositions and Therapeutic Uses

One object of this invention is to provide $VEGF_{145}$ in a pharmaceutical composition suitable for therapeutic use. Thus, in one aspect the invention provides a method for stimulating vascular cell proliferation in a patient by administering a therapeutically effective amount of pharmaceutical composition comprising $VEGF_{145}$.

By "therapeutically effective amount" is meant an amount of a compound that produces the desired therapeutic effect in a patient. For example, in reference to a disease or disorder, it is the amount which reduces to some extent one or more symptoms of the disease or disorder, and returns to normal, either partially or completely, physiological or biochemical parameters associated or causative of the disease or disorder. When used to therapeutically treat a patient it is an amount expected to be between 0.1 mg/kg to 100 mg/kg, preferably less than 50 mg/kg, more preferably less than 10 mg/kg, more preferably less than 1 mg/kg. The amount of compound depends on the age, size, and disease associated with the patient.

The optimal formulation and mode of administration of compounds of the present application to a patient depend on factors known in the art such as the particular disease or disorder, the desired effect, and the type of patient. While the compounds will typically be used to treat human patients, they may also be used to treat similar or identical diseases in other mammals such as other primates, farm animals such as swine, cattle and poultry, and sports animals and pets such as horses, dogs and cats.

Preferably, the therapeutically effective amount is provided as a pharmaceutical composition. A pharmacological agent or composition refers to an agent or composition in a form suitable for administration into a multicellular organism such as a human. Suitable forms, in part, depend upon the use or the route of entry, for example oral, transdermal, or by injection. Such forms should allow the agent or composition to reach a target cell whether the target cell is present in a multicellular host or in culture. For example, pharmacological agents or compositions injected into the blood stream should be soluble. Other factors are known in the art, and include considerations such as toxicity and forms which prevent the agent or composition from exerting its effect.

The claimed compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfonate, sulfamate, sulfate, acetate, citrate, lactate, tartrate, methanesulfonate, ethanesulfonate, benzenesulfonate, p-toluenesulfonate, cyclolexylsulfonate, cyclohexylsulfamate and quinate. Pharmaceutically acceptable salts can be obtained from acids such as hydrochloric acid, sulfuric acid, phosphoric acid, sulfonic acid, sulfamic acid, acetic acid, citric acid, lactic acid, tartaric acid, malonic acid, methanesulfonic acid, ethanesulfonic acid, benzenesulfonic acid, p-toluenesulfonic acid, cyclcohexylsulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The compounds of the invention can be formulated for a variety of modes of administration, including systemic and topical or localized administration. Techniques and formulations generally may be found in *Remington's Pharmaceutical Sciences*, 18th Edition, Mack Publishing Co., Easton, Pa., 1990. See also, Wang, Y. J. and Hanson, M. A. "*Parenteral Formulations of Proteins and Peptides: Stability and Stabilizers*", *Journal of Parenteral Science and Technology*, Technical Report No. 10, Supp. 42:2S (1988). A suitable administration format may best be determined by a medical practitioner for each patient individually.

For systemic administration, injection is preferred, e.g., intramuscular, intravenous, intraperitoneal, subcutaneous, intrathecal, or intracerebroventricular. For injection, the compounds of the invention are formulated in liquid solutions, preferably in physiologically compatible buffers such as Hank's solution or Ringer's solution. Alternatively, the compounds of the invention are formulated in one or more excipients (e.g., propylene glycol) that are generally accepted as safe as defined by USP standards. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery. In addition, the compounds may be formulated in solid form and redissolved or suspended immediately prior to use. Lyophilized forms are also included.

An inflatable balloon catheter with $VEGF_{145}$ protein coating the balloon may also be employed to deliver the substance to a targeted artery.

Alternatively, the compounds may be administered orally. For oral administration, the compounds are formulated into conventional oral dosage forms such as capsules, tablets and tonics.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be, for example, through nasal sprays or using suppositories. For oral administration, the molecules are formulated into conventional oral administration dosage forms such as capsules, tablets, and liquid preparations.

For topical administration, the compounds of the invention are formulated into ointments, salves, gels, or creams, as is generally known in the art.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

The amounts of various compounds of this invention to be administered can be determined by standard procedures. Generally, a therapeutically effective amount is between about 1 nmole and 3 µmole of the molecule, preferably between about 10 nmole and 1 µmole depending on the age and size of the patient, and the disease or disorder associated with the patient. Generally, it is an amount between about 0.1 and 50 mg/kg, preferably 1 and 20 mg/kg of the animal to be treated.

For use by the physician, the compositions will be provided in dosage unit form containing an amount of a $VEGF_{145}$.

Gene Therapy $VEGF_{145}$ will also be useful in gene therapy (reviewed in Miller, *Nature* 357:455–460 (1992)). Miller states that advances have resulted in practical approaches to human gene therapy that have demonstrated positive initial results. The basic science of gene therapy is described in Mulligan, *Science* 260:926–931 (1993). One example of gene therapy is presented in Example VII, which describes the use of adenovirus-mediated gene therapy.

As another example, an expression vector containing the $VEGF_{145}$ coding sequence may be inserted into cells, the cells are grown in vitro and then infused in large numbers into patients. In another example, a DNA segment containing a promoter of choice (for example a strong promoter) is transferred into cells containing an endogenous $VEGF_{145}$ in such a manner that the promoter segment enhances expression of the endogenous $VEGF_{145}$ gene (for example, the promoter segment is transferred to the cell such that it becomes directly linked to the endogenous $VEGF_{145}$ (gene).

The gene therapy may involve the use of an adenovirus vector including a nucleotide sequence coding for $VEGF_{145}$, or a naked nucleic acid molecule coding for $VEGF_{145}$. Alternatively, engineered cells containing a nucleic acid molecule coding for $VEGF_{145}$ may be injected. Example VII illustrates a method of gene therapy using an adenovirus vector to provide angiogenesis therapy.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant $VEGF_{145}$ into the targeted cell population. Methods which are well known to those skilled in the art can be used to construct recombinant viral vectors containing coding sequences. See, for example, Nabel, E. G., *Circulation,* 91, 541–548 (1995), the techniques described in Maniatis et al., *Molecular Cloning: A Laboratory Manual,* Cold Spring Harbor Laboratory, N.Y. (1989), and in Ausubel et al., *Current Protocols in Molecular Biology,* Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See Miller, *Nature* 357:455–60, 1992.

In its simplest form, gene transfer can be performed by simply injecting minute amounts of DNA into the nucleus of a cell, through a process of microinjection. Capecchi, M. R., *Cell* 22:479–88 (1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen, C. and Okayama, H., *Mol. Cell Biol.* 7:2745–52

(1987)); electroporation, wherein cells are exposed to large voltage pulses to introduce holes into the membrane (Chu, G. et al., *Nucleic Acids Res.*, 15:1311–26 (1987)); lipofection/liposome fusion, wherein DNA is packaged into lipophilic vesicles which fuse with a target cell (Felgner, P. L., et al., *Proc. Natl. Acad. Sci.* USA. 84:7413–7 (1987)); and particle bombardment using DNA bound to small projectiles (Yang, N. S., et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel, D. T., et al., *Am. J. Respir. Cell. Mol. Biol.*, 6:247–52 (1992).

A balloon catheter, such as those used in angioplasty, may be employed wherein the balloon is coated with the $VEGF_{145}$ DNA or vectors as described in Riessen, R., *Human Gene Therapy*, 4, 749–758 (1993) incorporated herein by reference.

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid molecule contact with a target cell by non-specific or receptor mediated interactions, uptake of nucleic acid molecule into the cell through the membrane or by endocytosis, and release of nucleic acid molecule into the cytoplasm from the plasma membrane or endosome. Expression may require, in addition, movement of the nucleic acid molecule into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid molecule or nucleic acid-protein complex into the patient.

In another preferred embodiment, a vector having nucleic acid molecule sequences encoding $VEGF_{145}$ is provided in which the nucleic acid molecule sequence is expressed only in a specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid molecule sequence which is capable of being expressed in vivo in an animal and thereby providing or augmenting the function of an endogenous gene which is missing or defective in the animal.

Clinical Applications

Stimulating angiogenesis in mammals by transfecting the endothelial cells with a polynucleotide coding for $VEGF_{145}$ may be accomplished, for example, according to the procedure described by Giordano et al. in "*Intracoronary Gene Transfer of Fibroblast Growth Factor-5 Increases Blood Flow an Contractile Function in an Ischemic Region of the Heart*", Nature Medicine, Vol. 2 No. 5, pp. 534–539, May 1996 which is incorporated herein by reference $VEGF_{145}$ will be released from cells infected by adenovirus vectors directing expression of $VEGF_{145}$ in cells of the heart. This releasability is also found in $VEGF_{121}$ and $VEGF_{165}$ but not in $VEGF_{189}$ or $VEGF_{206}$. However, $VEGF_{145}$ in contrast to $VEGF_{121}$ or $VEGF_{165}$, will be partially retained by ECM molecules as it diffuses towards target endothelial cells in adjacent blood vessels. The bound $VEGF_{145}$ may be slowly released later thus prolonging the angiogenic effect as compared to $VEGF_{121}$ or $VEGF_{165}$. Furthermore, the ECM bound $VEGF_{145}$ is active, and will support the newly synthesized blood vessels during the critical period of blood vessel maturation, until the existence of blood vessels is no longer dependent upon the presence of angiogenic growth factors. Thus, $VEGF_{145}$ will be more effective than any other VEGF form as a therapeutic agent to be used for induction of collateral blood vessels. These advantages may be critical when usage of adenovirus based expression vectors for gene therapy delivery of angiogenic agents is considered. An advantage of using adenovirus based vectors is that they are generally safe. The virus is lost quickly after the initial infection, and this is accompanied with a decrease in the production of the recombinant protein (Kass-Eisler, A., et. al. *Proc. Natl. Acad. Sci. USA* 90, 11498–11502, 1993). Because the $VEGF_{145}$ binding characteristics allow it to clear at a slower rate compared to other secreted VEGF forms, we anticipate $VEGF_{145}$ to be a more effective therapeutic agent compared to the other VEGF forms.

Balloon angioplasty is a major treatment of ischemic heart disease which involves the inflation of a balloon in a clogged blood vessel in order to open the blocked blood vessel. Unfortunately, this method of treatment frequently results in injury to the endothelial cells lining the inner walls of blood vessels. Smooth muscle cells often infiltrate into the opened blood vessels causing a secondary obstruction in a process called restenosis. $VEGF_{145}$ may be employed to induce proliferation of the endothelial cells located at the periphery of the balloon induced damaged area in order to cover the luminal surface of the vessel with a new monolayer of endothelial cells, hoping to restore the original structure of the blood vessel. Adenovirus mediated gene-therapy may also be applicable in this case as a method aimed at the delivery of inducers of endothelial cells proliferation to the lesion created by the balloon angioplasty procedure. The ability to bind to the ECM may offer several advantages for this application.

To prevent restenosis following balloon angioplasty, two types of approaches may be considered. It is possible to deliver a protein, or deliver an expression vector which will direct the expression of such a protein to the site of occlusion using the balloon that is used to open the clogged vessel. Such a protein will also inhibit the proliferation of the non-endothelial cells which invade the reopened blood vessel until the endothelial cells on both sides of the wounded endothelial cells monolayer have a chance to re-grow. This can be combined with the delivery of a protein or a vector such as a recombinant adenovirus which will speed the re-growth of the endothelial cell layer. However, growth factors such as FGF-5, bFGF or HGF are also mitogenic to smooth muscle cells, and will induce their proliferation, which is the opposite of the desired effect. VEGFs on the other hand are specific for endothelial cells. VEGF$_{145}$ will be especially useful in this context, because of its ECM binding properties. Following application, for example, by infection of adjacent cells with adenovirus encoding the protein, direct transfection with plasmid DNA encoding the protein, or the direct delivery of the protein, VEGF$_{145}$ will stick to the exposed extracellular matrix in the balloon treated vessel, and will promote proliferation and re-growth of endothelial cells specifically at the site of the lesion. Thus, VEGF$_{145}$ will localize and concentrate in the very region where its activity is required, making it a particularly attractive candidate for the treatment of restenosis.

Coronary angioplasty is frequently accompanied by deployment of an intravascular stent to help maintain vessel function and avoid restenosis. Stents have been coated with heparin to prevent thrombosis until the new channel formed by the stent can endothelialize. VEGF$_{145}$ can be applied directly to the stent, or nucleic acids encoding VEGF$_{145}$ such as plasmids, cDNA, or adenovirus vectors, may be applied to the stent for direct transfection of neighboring cells, using methods known to those of skill in the art. VEGF$_{145}$ that is locally applied, or produced through transfection, will enhance endothelialization of the stent and thus reduce thrombosis and re-stenosis.

Other applications for use of the growth factor of the present invention are contemplated. One example is for the treatment of ulcers. An ulcer is in effect a wound residing in the stomach. It was shown that angiogenic growth factors may be effective for the treatment of duodenal ulcers, and that stabilization of angiogenic growth factors may be a mechanism by which some therapeutic agents such as sucralfate produce their beneficial effects (Szabo, S., et. al. *Gastroenterology* 106, 1106–1111, 1994). Since VEGF is an angiogenic growth factor that is very stable under acidic conditions, its employment for the treatment of stomach and duodenal ulcers is contemplated. The heparin binding ability of VEGF$_{145}$ which acts to preserve it in an active state, and its expected ability to bind to exposed ECM at the wound site, indicate that VEGF$_{145}$ may be more suitable than other VEGF forms for treating stomach and duodenal ulcers.

To assist in understanding the present invention, the following Examples are included that describe the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE I

Isolation and Characterization of VEGF$_{145}$

Reverse PCR analysis of mRNA from OC-238 human epithelial ovarian carcinoma cells as well as HeLa cells and A431 cells (FIG. 5) detected a VEGF mRNA form corresponding in size to the predicted size of a VEGF mRNA form encodind a putative mature protein of 145 amino-acids. A reverse PCR product from OC-238 cells was sequenced and found to contain the exon structure 1–5, 6a, 8 which is the expected structure of a mRNA encoding VEGF$_{145}$. The cDNA which was sequenced was obtained using the primers GGAGAGATGAGCTTCCTACAG and TCACCGCCTTGGCTTGTCACA, corresponding to the sequences encoding amino-acids 92–98 of VEGF (common to all VEGF forms) and to the six carboxyl-terminal amino-acids of VEGF encoded by exon 8 of the VEGF gene. In all these cell lines the putative 145 amino acid-encoding cDNA appeared to be expressed at levels comparable to those of VEGF$_{165}$ and higher than those of VEGF$_{189}$. The mRNA encoding this VEGF form was not detected in several other transformed cell lines such as C6 glioma cells and U937 cells. Sequence analysis of the putative PCR product from the OC-238 cells showed that the mRNA contains exons 1–5, 6 and 8 of the VEGF gene in sequence (VEGF$_{145}$).

In order to produce recombinant VEGF$_{145}$ we prepared a VEGF$_{145}$ cDNA construct by deleting the oligonucleotides encoded by exon 7 out of VEGF$_{189}$ cDNA. Primers used to amplify exons 1–6 of the VEGF cDNA were the external primer, GCTTCCGGCTCGTATGTTGTGTGG, corresponding to a puc118 sequence and the internal primer, ACGCTCCAGGACTTATACCGGGA, corresponding to a sequence at the 3' end of exon 6. Primers used to amplify the 3' end of the VEGF cDNA were complementary to the puc118 sequence GGTAACGCCAGGGTTTTCCCAGTC and to the 3' end of the exon-6 sequence (underlined) and to the start of exon 8 (CGGTATAAGTCCTGGAGCGT-ATGTGACAAGCCGAGGCGGTGA). Following amplification, the PCR products were precipitated, and the products re-amplified using only the puc118 derived external primers. The product was gel purified, subcloned into the PCR-II vector and sequenced using the Sequenase-II kit obtained from U.S. Biochemical Corp. (Cleveland, Ohio). This cDNA was further used for protein expression studies.

Figure 4A:
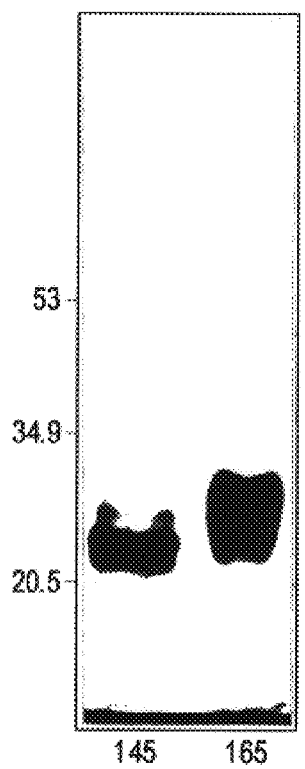
FIGS. 4(A–B) is a photograph showing expression of reduced and non-reduced recombinant $VEGF_{145}$ and comparison to $VEGF_{145}$. $VEGF_{145}$ and $VEGF_{165}$ were produced in Sf9 insect cells infected by recombinant baculoviruses encoding $VEGF_{145}$ and $VEGF_{165}$ as indicated. Conditioned medium containing recombinant VEGF was collected, and 10 μl aliquots were either reduced using 0.1 M dithiotreitol (panel A) or not reduced (panel B). Proteins were separated by SDS/PAGE (12% gel) and transferred by electroblotting to nitrocellulose. Filters were blocked for 1 h at room temperature with buffer containing 10 mM tris/HCl pH 7.0.15M NaCl, and 0.1% Tween 20 (TBST) supplemented with 10% low-fat milk. The filters were incubated for 2 hours at room temperature with rabbit anti-VEGF polyclonal antibodies in TBST (23), washed three times with TBST, and incubated with anti-rabbit IgG peroxidase conjugated antibodies for 1 h at room temperature. Bound antibody was visualized using the ECL detection system.
Figure 4B:
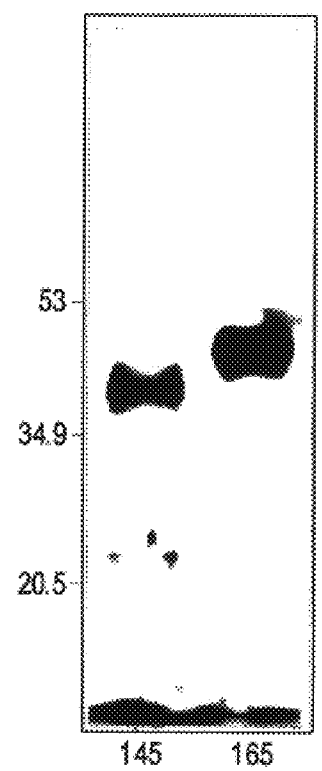
Figure 6:
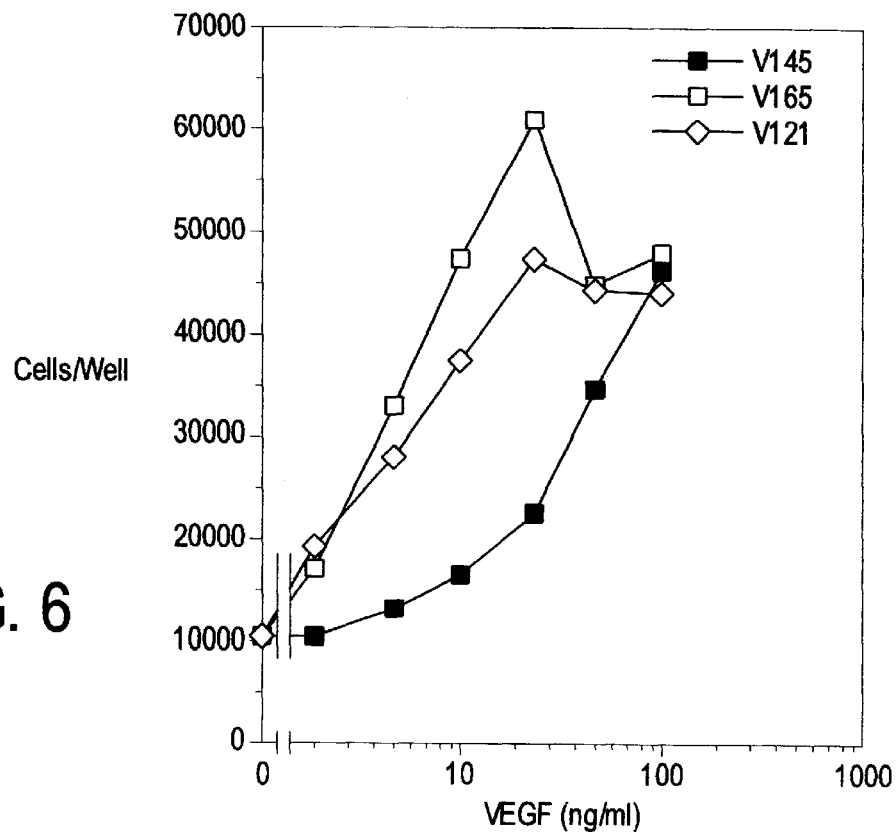
FIG. 6 is a graph that describes an experiment showing that recombinant $VEGF_{145}$ is mitogenic to vascular endothelial cells. $VEGF_{145}$ stimulates the proliferation of endothelial cells: HUVEC cells were seeded in 24 well dishes (20,000 cells/well), and increasing concentrations of $VEGF_{121}$ (◊), $VEGF_{145}$ (■) and $VEGF_{165}$ ( ) were added every other day as described in materials and methods. Cells were counted in a Coulter counter after 4 days.

This recombinant VEGF$_{145}$ cDNA was used to construct a recombinant baculovirus containing the VEGF$_{145}$ cDNA. The virus was used to infect Sf9 cells as described for VEGF$_{165}$ by Cohen, T., et. al. *Growth Factors.* 7:131–138, 1992, incorporated herein by reference. Most of the VEGF$_{145}$ produced by the infected Sf9 cells was found in the conditioned medium as a homodimer of ~41 kDa, with small amounts of monomeric VEGF$_{145}$ (FIG. 4). The VEGF$_{145}$ dimers dissociated into monomers upon reduction with dithiotreitol. VEGF$_{145}$ was partially purified using heparin-sepharose. The protein was eluted from the column using a stepwise salt gradient. Most of the VEGF$_{145}$ was eluted at 0.6–0.7 M NaCl, indicating that the heparin binding affinity of VEGF$_{145}$ is similar to that of VEGF$_{165}$. The recombinant VEGF$_{145}$ was biologically active and induced the proliferation of human umbilical vein derived endothelial cells (HUVEC cells). The ED$_{50}$ of VEGF$_{145}$ was 30 ng/ml, whereas the ED$_{50}$ of VEGF$_{165}$ was 6 fold lower (FIG. 6).

EXAMPLE II

Proliferation of Endothelial Cells and Angiogenesis

To confirm that VEGF$_{145}$ can induce angiogenesis in vivo, the VEGF$_{145}$ cDNA was subcloned into the Bam-HI site of the mammalian expression vector MIRB using the technique described by Macarthur, C. A., et. al. *Cell Growth Differ.* 6, 817–825, 1995, which is incorporated herein by reference. The MIRB/VEGF$_{145}$ plasmid was transfected into BHK-21 hamster kidney derived cells, and stable cell lines producing VEGF$_{145}$ isolated. The VEGF$_{145}$ produced by the mammalian cells was biologically active and was secreted into the growth medium. A stable clone producing 0.1 mg VEGF$_{145}$ per $10^6$ cells was isolated. The VEGF$_{145}$ expressing cells were embedded in alginate beads, and the beads were implanted under the skin of balb/c mice using the method described by Plunkett, M. L., et. al. *Lab. Invest.* 62, 510–517, 1990, which is incorporated herein by reference.

Alginate pellets containing the entrapped cells were removed after four days and photographed (FIG. 11). Clusters of alginate beads containing $VEGF_{145}$-expressing cells were dark red with blood, while beads containing cells transfected with vector alone had a much lower content of blood. When examined under higher magnification, pellets containing $VEGF_{145}$ producing cells appeared much more vascularized than pellets containing control cells. These results are consistent with the expected behavior of an vascular cell proliferation or angiogenesis-promoting factor.

EXAMPLE III

Figure 1:
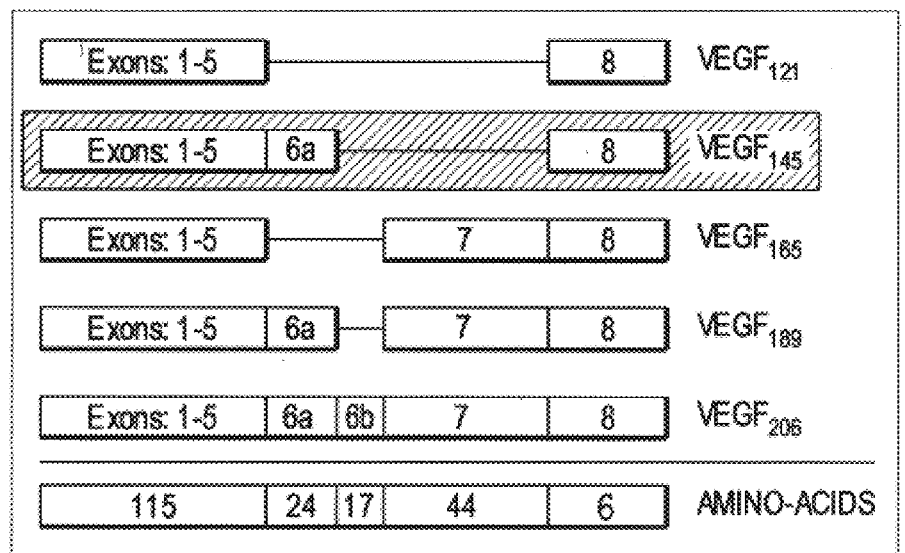
FIG. 1 is a graphic depiction of the exons that encode various VEGF isoforms.
Figure 7:
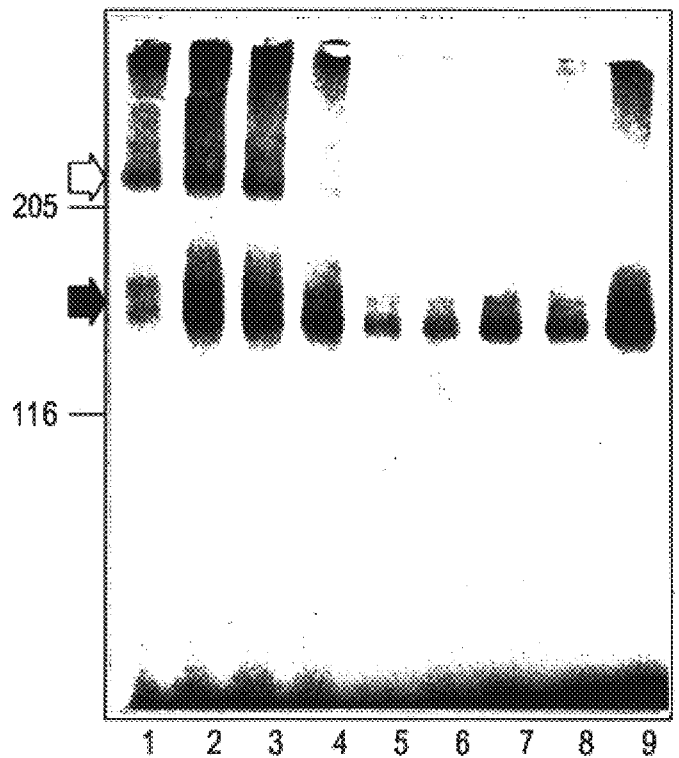
FIG. 7 is a photograph of an experiment showing that $VEGF_{145}$ binds to the KDR/flk-1 VEGF receptor but not to two $VEGF_{165}$ specific VEGF receptors found on vascular endothelial cells. Effect of $VEGF_{145}$ on $^{125}I$-$VEGF_{165}$ binding to endothelial cells. $^{125}I$-$VEGF_{165}$ (10 ng/ml) was bound to confluent HUVEC cells grown in 5 cm dishes for 2 h at 4° C. in the presence of 1 μg/ml heparin and the increasing concentrations of $VEGF_{145}$ (μg/ml): Lane 1, 0; Lane 2, 0.05; Lane 3, 0.1; Lane 4, 0.25; Lane 5, 0.5; Lane 6, 1; Lane 7, 2; Lane 8, 3. Lane 9 received 2 mg/ml of $VEGF_{121}$. Bound $^{125}I$-VEGF165 was subsequently cross-linked to the cells using DSS, and cross-linked complexes were visualized by autoradiography.

Receptor Binding Characteristics $VEGF_{165}$ binds to three VEGF receptors on HUVEC cells while $VEGF_{121}$ only binds to the larger of these receptors. The common receptor to which both $VEGF_{121}$ and $VEGF_{165}$ bind is the KDR/flk-1 VEGF receptor (Gitay-Goren, H., et. al. *J. Biol. Chem.* 271, 5519–5523, 1996). In order to determine the receptor recognition pattern of $VEGF_{145}$. $^{125}I\text{-}VEGF_{165}$ (produced as described in Gitay-Goren, H., et. al. *J. Biol. Chem.* 271, 5519–5523, 1996, incorporated by reference herein) was bound to HUVEC cells in the presence of 1 μg/ml of heparin and increasing concentrations of $VEGF_{145}$. Bound $^{125}I\text{-}VEGF_{165}$ was subsequently covalently cross-linked to the VEGF receptors. $VEGF_{145}$ inhibited the binding of $^{125}I\text{-}VEGF_{165}$ to the KDR/flk-1 receptor of the HUVEC cells but not to the two smaller $VEGF_{165}$ specific receptors of the cells (FIG. 7). This result was verified in a cell free binding experiment in which $VEGF_{145}$ competed with $^{125}I\text{-}VEGF_{165}$ for binding to a soluble fusion protein containing the extracellular domain of the flk-1 receptor. In contrast, $VEGF_{145}$ competed rather ineffectively with $^{125}I\text{-}VEGF_{165}$ for binding to the two smaller VEGF receptors, indicating that the affinity of $VEGF_{145}$ towards these two receptors is substantially lower than that of $VEGF_{165}$. It follows that the behavior of $VEGF_{145}$ differs from that of $VEGF_{165}$. The presence of exon-6 is not sufficient to enable efficient binding of $VEGF_{145}$ to these two receptors, despite the heparin binding properties that exon-6 confers on $VEGF_{145}$.

EXAMPLE IV

Figure 8A:
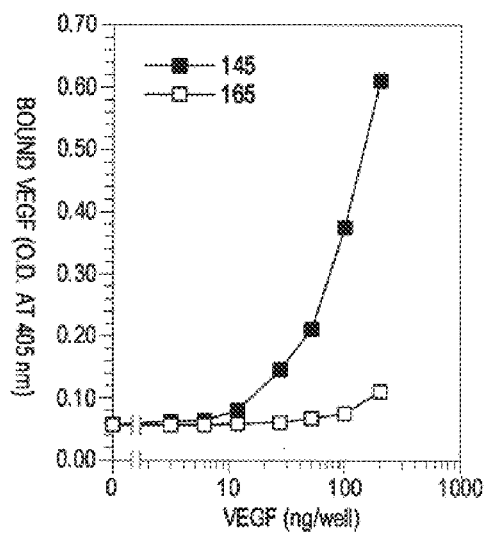
FIGS. 8(A–C) describes two experiments showing that $VEGF_{145}$ binds to the ECM produced by bovine corneal endothelial cells but $VEGF_{165}$ does not.
Figure 8B:
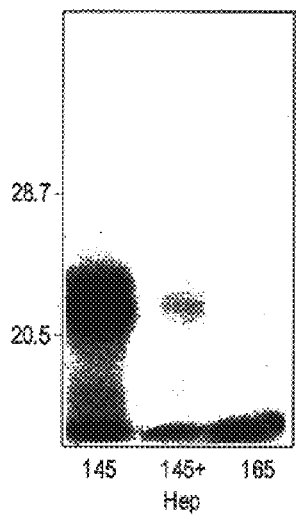
Figure 8C:
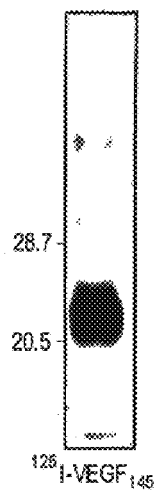

ECM Binding Characteristics $VEGF_{189}$ binds efficiently to the ECM produced by CEN4 cells, while $VEGF_{165}$ binds to it very weakly and $VEGF_{121}$ does not bind to it at all. The fact that $VEGF_{189}$ bind heparin with high affinity led to the suggestion that the interaction of $VEGF_{189}$ with the ECM is mediated by heparin-sulfate proteoglycans (Houck, K. A., et al., *J. Biol. Chem.* 267, 26031–26037 (1992); Park, J. E., et al., *Mol. Biol. Cell* 4, 1317–1326 (1993)). The heparin binding affinities of $VEGF_{145}$ and $VEGF_{165}$ are similar, and substantially lower than the heparin binding affinity of $VEGF_{189}$ and $VEGF_{145}$ was therefore expected to bind poorly to ECM. Surprisingly, experiments in which $VEGF_{145}$ was bound to an ECM produced by bovine corneal endothelial cells showed that $VEGF_{145}$ bound efficiently whereas the binding of $VEGF_{1}65$ was marginal. In these experiments, the results of which are shown in FIG. 8, it can be seen that $VEGF_{145}$ binds efficiently to the ECM while $VEGF_{165}$ binds much less efficiently if at all. The binding of $^{125}I\text{-}VEGF_{145}$ to the ECM was substantially, but not completely, inhibited by 10 g/ml heparin. The $^{125}I\text{-}VEGF_{145}$ used in these experiments contained some impurities, but the major iodinated protein that was recovered from the ECM had a mass corresponding to that of $^{125}I\text{-}VEGF_{145}$ (see FIG. 8b). To make sure that $^{125}I\text{-}VEGF_{145}$ binds to the ECM and not to exposed plastic surfaces, the ECM was scraped off, washed by centrifugation, and the amount of adsorbed $^{125}I\text{-}VEGF_{145}$ in the pellet determined. The ECM contained ~70% of the adsorbed $^{125}I\text{-}VEGF_{145}$. Based on the aforementioned, we believe that the presence of the exon-6 derived peptide in $VEGF_{145}$ enables efficient binding to the ECM, while the exon-7 derived peptide of $VEGF_{165}$ does not provide this property. Thus, $VEGF_{145}$ differs substantially in this respect from $VEGF_{121}$ or $VEGF_{165}$.

EXAMPLE V

ECM Binding Characteristics

Figure 9A:
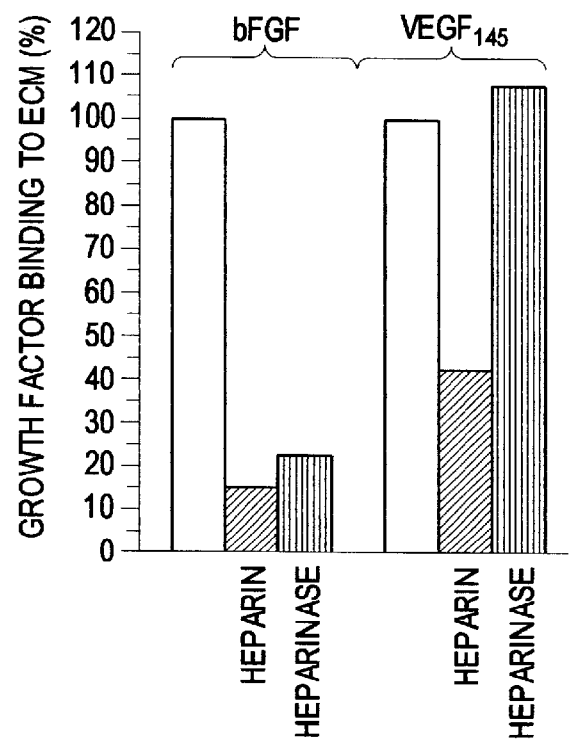

The above described experiments indicated that $VEGF_{145}$ binds to the ECM while $VEGF_{165}$ binds to it much less effectively. $VEGF_{145}$ and $VEGF_{165}$ bind with similar affinities to heparin suggesting that the binding to the ECM is not mediated by heparin-like molecules. The interaction of bFGF with the ECM is mediated by heparin-sulfate proteoglycans. To determine whether $VEGF_{145}$ interacts with the ECM using a bFGF like binding mechanism, $^{125}I\text{-}VEGF_{145}$ was bound to ECM coated dishes in the presence of 10 μg/ml heparin. The binding of $VEGF_{145}$ was inhibited by ~60% while the binding of $^{125}I$-bFGF to the ECM was inhibited by 80%. The binding of $^{125}I\text{-}VEGF_{145}$ to the ECM was also inhibited by 80% in the presence of 0.8 M salt, indicating that the interaction is not hydrophobic. These results are compatible with the expected behavior of proteins that bind to the ECM via heparin-like molecules. However, we unexpectedly observed that $^{125}I\text{-}VEGF_{145}$ was also able to bind efficiently to an ECM that was digested with heparinase-II. In contrast, there was almost no binding of $^{125}I$-bFGF to the heparinase-II treated ECM (FIG. 9a). This observation indicates that $VEGF_{145}$ does not bind to the ECM by binding to ECM associated heparin-like molecules.

Figure 9B:
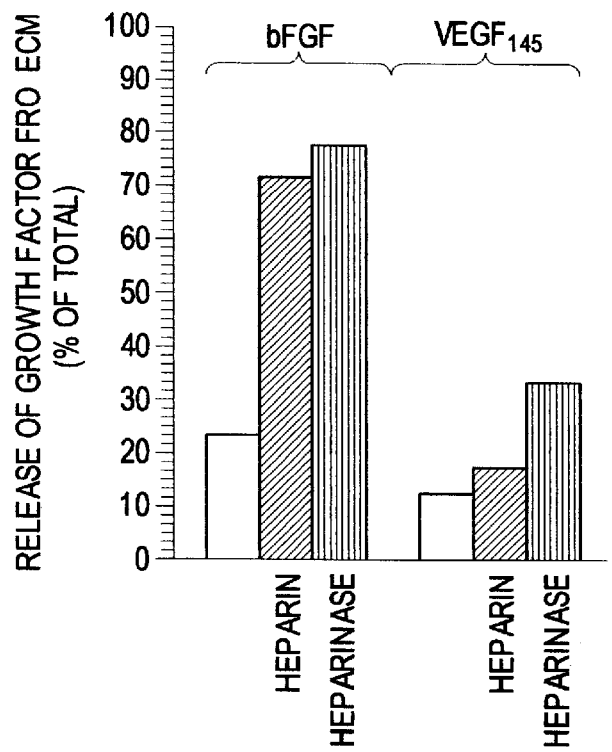

In order to further investigate the mode of interaction of $VEGF_{145}$ with the ECM, we tested the ability of heparin and heparinase treatment to release pre-bound $VEGF_{145}$ from the ECM. Similar differences were observed when ECM containing bound $^{125}I\text{-}VEGF_{145}$ or $^{125}I$-bFGF was incubated with heparin or digested with heparinase-II. When the ECM coated wells were incubated for two hours at 37° C. with binding buffer, 20% of the bound $^{125}I$-bFGF and 13% of the bound $^{125}I\text{-}VEGF_{145}$ dissociated from the ECM. This release may be attributed in part to a proteolytic activity residing in the ECM. When 10 μg/ml heparin were included in the buffer, only 33% of $^{125}I\text{-}VEGF_{145}$ was released from the matrix, as compared with the release of 78% of prebound $^{125}I$-bFGF. An even sharper difference was observed when heparinase-II was added to the binding buffer. The enzyme released 72% of the bound $^{125}I$-bFGF, but only 17% of the bound $^{125}I\text{-}VEGF_{145}$ (FIG. 9b). Similar results were obtained when the experiment was performed with unlabeled $VEGF_{145}$ using a commercial monoclonal anti-VEGF antibody to detect VEGF bound to the ECM.

To assess the efficiency of the heparinase-II digestion, the ECM was metabolically labeled with $^{35}S$-sulfate and the labeled ECM was digested with heparinase-II. The digestion released 80–85% of the labeled sulfate residues. To determine whether $VEGF_{145}$ can bind to ECM depleted of sulfated glycosaminoglycans, BCE cells were grown in the presence of 30 mM chlorate, an inhibitor of glycosarninoglycan sulfation in the manner described by Miao, H. Q., et. al. *J. Biol Chem* 271, 4879–4886, 1996. ECM's produced in the presence or absence of chlorate, were further digested with a mixture of heparinases I, II and III. Neither of these treatments inhibited significantly the binding of $VEGF_{145}$ to the ECM, despite a >95% decrease in the content of sulfate moieties in the ECM.

The ECM produced by BCE cells contains bFGF, which is mitogenic for endothelial cells. However, endothelial cells do not proliferate when they are seeded on ECM produced in the presence of chlorate since bFGF does not bind to ECM depleted of sulfated heparin-like molecules. $VEGF_{145}$ binds to ECM produced in the presence of chlorate, and we therefore examined whether $VEGF_{145}$ bound to such ECM retains its biological activity. Wells coated with ECM produced in the presence of chlorate were incubated with increasing concentrations of either $VEGF_{145}$ or $VEGF_{165}$. The wells were subsequently washed extensively and HUVEC cells were seeded in the wells. ECM incubated with $VEGF_{145}$ induced proliferation of vascular endothelial cells while ECM incubated with $VEGF_{165}$ did not, indicating ECM associated $VEGF_{145}$ is biologically active (FIG. 10).

EXAMPLE VI

Comparison of VEGF,4–5 with Other VEGF Forms heparinase. Thus despite the similar heparin-binding affinities of $VEGF_{165}$ and $VEGF_{145}$ surprisingly, $VEGF_{145}$ is secreted and binds efficiently to the ECM, unlike $VEGF_{165}$.

b. Comparison with $VEGF_{121}$ $VEGF_{121}$ does not contain exons 6 and 7 of the VEGF gene. In contrast to VEGF $VEGF_{121}$ does not bind to heparin. Like $VEGF_{145}$, $VEGF_{121}$ does not bind to the two smaller VEGF receptors found in the endothelial cells and in various types of cancer cells. Both $VEGF_{121}$ and $VEGF_{145}$ are secreted from cells, but $VEGF_{121}$ does not bind to the ECM. $VEGF_{121}$ is inactivated by oxidation like $VEGF_{165}$ and $VEGF_{145}$ but the activity of $VEGF_{121}$ is not restored by binding to heparin-like molecules.

c. Comparison with $VEGF_{189}$ and $VEGF_{206}$ $VEGF_{189}$ contains peptides encoded by exon-6 and by exon 7 of the VEGF gene. It binds to heparin with a higher affinity as compared to $VEGF_{145}$. It also binds very well to the ECM. However, unlike $VEGF_{145}$, $VEGF_{189}$ is not secreted into the medium of $VEGF_{189}$ producing cells and remains cell associated. The properties of $VEGF_{206}$ are similar to those of $VEGF_{189}$.

Although heparin is able to release $VEGF_{145}$ from ECM, as observed for $VEGF_{189}$, it is likely that $VEGF_{145}$ does not

TABLE 1

Overview of differences between $VEGF_{145}$ and the other VEGF forms.

| | $VEGF_{121}$ | $VEGF_{145}$ | $VEGF_{165}$ | $VEGF_{189}$ | $VEGF_{206}$ |
|---|---|---|---|---|---|
| Exons | 1–5, 8 | 1–5, 6a, 8 | 1–5, 7, 8 | 1–5, 6a, 7, 8 | 1–5, 6b, 7, 8 |
| Mitogen for endothelial cells | + | + | + | + | + |
| Angiogenic activity | + | + | + | n.d. | n.d. |
| Binding to Flk-1 and Flt-1 receptors | + | + | + | n.d. | n.d. |
| Binding to two small VEGF receptors of endothelial cells | – | – | + | n.d. | n.d. |
| Binding to ECM | – | + | – | + | + |
| Protection against oxidative Damage by heparin-like molecules | – | + | + | n.d. | n.d. |
| Secretion from producing cells | + | + | + | – | – | a. Comparison with $VEGF_{165}$ $VEGF_{165}$ contains exons 1–5, 7 and 8 of the VEGF gene, and lacks exon 6. It binds heparin with an affinity similar to that of $VEGF_{145}$. $VEGF_{145}$ binds to a single VEGF receptor on human umbilical vein derived endothelial cells, which was identified as the KDR/flk-1 VEGF receptor. In contrast, $VEGF_{165}$ binds to two additional high affinity receptors which are present on vascular endothelial cells and on several other cell types (Neufeld, G., et. al. *Cancer Metastasis Rev.* 15:153–158, 1996). It is not clear yet if thes $VEGF_{165}$ binding, but if they do, than endothelial cells should display a more restricted biological response to $VEGF_{145}$ as compared to $VEGF_{165}$. $VEGF_{165}$ is susceptible to oxidative agents. These are especially abundant in inflamed tissue and in situations such as wounding. However, when $VEGF_{165}$ damaged by oxidation binds to heparin-like molecules found on endothelial cells the activity of the damaged $VEGF_{165}$ is restored (Gitay-Goren, H., et. al. *J. Biol. Chem.* 271, 5519–5523, 1996). This property is also shared by $VEGF_{145}$. In addition, $VEGF_{165}$ binds very weakly to ECM, if at all. The residual binding of $VEGF_{165}$ to the ECM is inhibited further following digestion of the ECM with heparinase. In contrast, the binding of $VEGF_{145}$ to the ECM is not altered by prior digestion of the ECM by use ECM resident heparin-sulfates to bind to the matrix. We have so far been unable to demonstrate an angiogenic response with intact $VEGF_{189}$. This may be due to the tight association of $VEGF_{189}$ with the $VEGF_{189}$ producing cells, and with the ECM found in close proximity to the $VEGF_{189}$ producing cells. In contrast, we have demonstrated that $VEGF_{145}$ is released from producing cells and promotes angiogenesis in-vivo. This observation indicates that the affinity of $VEGF_{145}$ to ECM is probably lower than that of $VEGF_{189}$. Thus, $VEGF_{145}$ possesses a unique combination of properties that may render it a more suitable therapeutic agent in certain situations as compared to other VEGF forms.

EXAMPLE VII

Gene-Transfer-Mediated Angiogenesis Therapy Using $VEGF_{145}$

DNA encoding $VEGF_{145}$ is used for gene-transfer-mediated angiogenesis therapy as described, for example, in International Patent Application No. PCT/US96/02631, published Sep. 6, 1996, as WO96/26742, hereby incorporated by reference herein in its entirety.

Adenoviral Constructs

A helper independent replication deficient human adenovirus 5 system may be used for gene-transfer. A nucleic acid molecule coding for $VEGF_{145}$ may be cloned into the polylinker of plasmid ACCMVPLPA which contains the CMV promoter and SV40 polyadenylation signal flanked by partial adenoviral sequences from which the E1A and E1B genes (essential for viral replication) have been deleted. This plasmid is co-transferred (lipofection) into 293 cells with plasmid JM17 which contains the entire human adenoviral 5 genome with an additional 4.3 kb insert making pJM17 too large to be encapsidated. Homologous rescue recombination results in adenoviral vectors containing the transgene in the absence of E1A/E1B sequences. Although these recombinants are nonreplicative in mammalian cells, they can propagate in 293 cells which have been transformed with E1A/E1B and provided these essential gene products in trans. Transfected cells are monitored for evidence of cytopathic effect which usually occurs 10–14 days after transfection. To identify successful recombinants, cell supernatant from plates showing a cytopathic effect is treated with proteinase K (50 mg/ml with 0.5% sodium dodecyl sulfate and 20 mM EDTA) at 56° C. for 60 minutes, phenol/chloroform extracted and ethanol precipitated. Successful recombinants are then identified with PCR using primers (*Biotechniques*, 15:868–72, 1993) complementary to the CMV promoter and SV40 polyadenylation sequences to amplify the $VEGF_{145}$ nucleic acid insert and primers (*Biotecniques*, 15:868–72, 1993) designed to concomitantly amplify adenoviral sequences. Successful recombinants then are plaque purified twice. Viral stocks are propagated in 293 cells to titers ranging between $10^{10}$ and $10^{12}$ viral particles, and are purified by double CsCl gradient centrifugation prior to use. The system used to generate recombinant adenoviruses imposed a packing limit of 5 kb for transgene inserts. The $VEGF_{145}$ genes, driven by the CMV promoter and with the SV40 polyadenylation sequences are well within the packaging constraints. Recombinant vectors are plaque purified by standard procedures. The resulting viral vectors are propagated on 293 cells to titers in the $10^{10}$–$10^{12}$ viral particles range. Cells are infected at 80% confluence and harvested at 36–48 hours. After freeze-thaw cycles the cellular debris is pelleted by standard centrifugation and the virus further purified by double CsCl gradient ultracentrifugation (discontinuous 1.33/1.45 CsCl gradient; cesium prepared in 5 mM Tris, 1 mM EDTA (pH 7.8); 90,000×g (2 hr), 105,000×g (18 hr)). Prior to in vivo injection, the viral stocks are desalted by gel filtration through Sepharose columns such as G25 Sephadex. The resulting viral stock has a final viral titer approximately in the $10^{10}$–$10^{12}$ viral particles range. The adenoviral construct should thus be highly purified, with no wild-type (potentially replicative) virus.

Porcine Ischemia Model for Angiogenesis

A left thoracotomy is performed on domestic pigs (30–40 kg) under sterile conditions for instrumentation. (Hammond, et al., *J Clin Invest* 92:2644–52, and Roth, et al., *J. Clin. Invest.* 91:939–49, 1993). Catheters are placed in the left atrium and aorta, providing a means to measure regional blood flow, and to monitor pressures. Wires are sutured on the left atrium to permit ECG recording and atrial pacing. Finally, an amaroid is placed around the proximal LCx. After a stable degree of ischemia develops, the treatment group receives an adenoviral construct that includes a $VEGF_{145}$ gene driven by a CMV promoter. Control animals receive gene transfer with an adenoviral construct that includes a reporter gene, lacZ, driven by a CMV promoter.

Studies are initiated 35±3 days after amaroid placement, at a time when collateral vessel development and pacing-induced dysfunction are stable (Roth, et al., *Am. J. Physiol* 253:1–11279–1288, 1987, and Roth, et al., *Circulation* 82:1778–89). Conscious animals are suspended in a sling and pressures from the LV, LA and aorta, and electrocardiogram are recorded in digital format on-line (at rest and during atrial pacing at 200 bpm). Two-dimensional and M-mode images are obtained using a Hewlett Packard ultrasound imaging system. Images are obtained from a right parasternal approach at the mid-papillary muscle level and recorded on VHS tape. Images are recorded with animals in a basal state and again during right atrial pacing (HR=200 bpm). These studies are performed one day prior to gene transfer and repeated 14±1 days later. Rate-pressure products and left atrial pressures should be similar in both groups before and after gene transfer, indicating similar myocardial oxygen demands and loading conditions. Echocardiographic measurements are made using standardized criteria (Sahn, et al., *Circulation* 58:1072, 1978). End-diastolic wall thickness (EDWTh) and end-systolic wall thickness (ESWTh) are measured from 5 continuous beats and averaged. Percent wall thickening (% WTh) is calculated [(EDWTh-ESWTh)/EDWTh]×100. Data should be analyzed without knowledge of which gene the animals had received. To demonstrate reproducibility of echocardiographic measurements, animals should be imaged on two consecutive days, showing high correlation ($r^2$=0.90; p=0.005).

35±3 days after amaroid placement, well after amaroid closure, but before gene transfer, contrast echocardiographic studies are performed using the contrast material (Levovist) which is injected into the left atrium during atrial pacing (200 bprn). Studies are repeated 14±1 days after gene transfer. Peak contrast intensity is measured from the video images using a computer-based video analysis program (Color Vue II, Nova Microsonics, Indianapolis, Ind.), that provides an objective measure of video intensity. The contrast studies are analyzed without knowledge of which gene the animals have received.

At completion of the study, animals are anesthetized and midline thoracotomy performed. The brachycephalic artery is isolated, a canula inserted, and other great vessels ligated. The animals receive intravenous heparin (10,000 IU) and papaverine (60 mg). Potassium chloride is given to induce diastolic cardiac arrest, and the aorta cross-clamped. Saline is delivered through the brachycephalic artery cannula (120 mmHg pressure), thereby perfusing the coronary arteries. Glutaraldehyde solution (6.25%, 0.1 M cacodylate buffer) was perfused (120 mmHg pressure) until the heart is well fixed (10–15 min). The heart is then removed, the beds identified using color-coded dyes injected anterograde through the left anterior descending (LAD), left circumflex (LCx), and right coronary arteries. The amaroid is examined to confim closure. Samples taken from the normally perfused and ischemic regions are divided into thirds and the endocardial and epicardial thirds are plastic-imbedded. Microscopic analysis to quantitate capillary number is conducted as previously described (Mathieu-Costello, et al., *Am. J. Physiol* 359:H204, 1990). Four 1 µm thick transverse sections are taken from each subsanple (endocardium and epicardium of each region) and point-counting is used to determine capillary number per fiber number ratio at 400× magnification. Twenty to twenty-five high power fields are counted per subsample. Within each region, capillary number to fiber number rations should be similar in endocardium and epicardium so the 40–50 field per region should be averaged to provide the transmural capillary to fiber number ratio.

To establish that improved regional function and blood flow result from transgene expression, PCIR and PT-PCR may be used to detect transgenic VEGF$_{145}$ DNA and mRNA in myocardium from animals that have received VEGF$_{145}$ gene transfer. Using a sense primer to the CMV promoter [GCAGAGCTCGTTTAGTGAAC] and an antisense primer to the internal VEGF$_{145}$ gene sequence PCIR is used to amplify the expected 500 bp fragment. Using a sense primer to the beginning of the VEGF$_{145}$ sequence and an antisense primer to the internal VEGF$_{145}$ gene sequence RT-PCR is used to amplify the expected 400 bp fragment.

Finally, using an antibody directed against VEGF$_{145}$. VEGF$_{145}$ protein expression may be demonstrated 48 hours as well as 14±1 days after gene transfer in cells and myocardium from animals that have received gene transfer with a VEGF$_{145}$ gene.

The helper independent replication deficient human adenovirus 5 system is used to prepare transgene containing vectors. The material injected in vivo should be highly purified and contain no wild-type (replication competent) adenovirus. Thus adenoviral infection and inflammatory infiltration in the heart are minimized. By injecting the material directly into the lumen of the coronary artery by coronary catheters, it is possible to target the gene effectively. When delivered in this manner there should be no transgene expression in hepatocytes, and viral RNA should not be found in the urine at any time after intracoronary injection.

Injection of the construct (4.0 ml containing about $10^{11}$ viral particles of adenovirus) is performed by injecting 2.0 ml into both the left and right coronary arteries (collateral flow to the LCx bed appeared to come from both vessels). Animals are anesthetized, and arterial access acquired via the right carotid by cut-down; a 5F Cordis sheath is then placed. A 5F Multipurpose (A2) coronary catheter is used to engage the coronary arteries. Closure of the LCx amaroid is confirmed by contrast injection into the left main coronary artery. The catheter tip is then placed 1 cm within the arterial lumen so that minimal material is lost to the proximal aorta during injection. This procedure is carried out for each of the pigs.

Once gene transfer is performed, three strategies are used to establish successful incorporation and expression of the gene: (1) Some constructs may include a reporter gene (lacZ); (2) myocardium from the relevant beds is sampled, and immunoblotting is performed to quantitate the presence of VEGF$_{145}$ protein; and (3) PCR is used to detect VEGF$_{145}$ mRNA and DNA.

The regional contractile function data obtained should show that control pigs show a similar degree of pacing-induced dysfunction in the ischemic region before and 14±1 days after gene transfer. In contrast, pigs receiving VEGF$_{145}$ gene transfer should show an increase in wall thickening in the ischemic region during pacing, demonstrating that VEGF$_{145}$ gene transfer in accordance with the invention is associated with improved contraction in the ischemic region during pacing. Wall thickening in the normally perfused region (the interventricular septum) should be normal during pacing and unaffected by gene transfer. The percent decrease in function measured by transthoracic echocardiography should be very similar to the percentage decrease measured by sonomicrometry during atrial pacing in the same model (Hammond, et al. *J. Clin. Invest.* 92:2644, 1993), documenting the accuracy of echocardiography for the evaluation of ischemic dysfunction.

Although preferred embodiments are specifically described herein, it will be appreciated that many modifications and variations of the present invention are possible in light of the above teachings and within the purview of the appended claims without departing from the spirit and intended scope of the invention.

What is claimed is:

1. An expression vector comprising a polynucleotide sequence encoding $VEGF_{145}$.

2. A filtered injectable adenovirus vector preparation, comprising: a recombinant adenoviral vector, said vector containing no wild-type virus and comprising:

a partial adenoviral sequence from which the EIA/EIB genes have been deleted, and a transgene coding for a $VEGF_{145}$, driven by a promoter flanked by the partial adenoviral sequence; and a pharmaceutically acceptable carrier.

3. The filtered injectable adenovirus vector preparation of claim 2, wherein the transgene coding for a $VEGF_{145}$ comprises the sequence of SEQ ID NO. 1.

4. The filtered injectable adenovirus vector preparation of claim 2, wherein the promoter is a CMV promoter.

5. The expression vector of claim 1, wherein the polynucleotide sequence encodes the amino acid sequence of SEQ ID NO. 2.

* * * * *